United States Patent
Kim et al.

(10) Patent No.: US 6,962,768 B2
(45) Date of Patent: Nov. 8, 2005

(54) ETHER MONOMERS AND POLYMERS HAVING MULTI-RING STRUCTURES, AND PHOTOSENSITIVE POLYMERS AND RESIST COMPOSITIONS OBTAINED FROM THE SAME

(75) Inventors: Hyun-Woo Kim, Hwaseong-si (KR); Sang-Gyun Woo, Yongin-si (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 19 days.

(21) Appl. No.: 10/799,025

(22) Filed: Mar. 12, 2004

(65) Prior Publication Data

US 2004/0170919 A1 Sep. 2, 2004

Related U.S. Application Data

(63) Continuation-in-part of application No. 10/132,804, filed on Apr. 24, 2002, now Pat. No. 6,713,228.

(30) Foreign Application Priority Data

Nov. 28, 2003  (KR) ................................ 10-2003-0085830

(51) Int. Cl.$^7$ ......................... G03F 7/039; C08F 34/02; C07D 311/78
(52) U.S. Cl. .................... 430/270.1; 430/905; 430/907; 430/914; 525/242; 525/245; 525/247; 549/386
(58) Field of Search ............................. 430/270.1, 905, 430/907, 914; 525/242, 245, 247; 549/386

(56) References Cited

U.S. PATENT DOCUMENTS

| | | | | |
|---|---|---|---|---|
| 5,380,659 A | * | 1/1995 | Holla et al. ................. | 435/196 |
| 6,517,990 B1 | * | 2/2003 | Choi et al. ............... | 430/270.1 |
| 6,787,287 B2 | * | 9/2004 | Kim et al. ............... | 430/270.1 |
| 2003/0215758 A1 | * | 11/2003 | Kim et al. ............... | 430/495.1 |

* cited by examiner

Primary Examiner—Yvette C. Thornton

(74) Attorney, Agent, or Firm—Harness, Dickey & Pierce, P.L.C.

(57) ABSTRACT

Provided are a variety of monomers suitable of producing photosensitive polymers, that are in turn, useful in photoresist compositions, through radical (cationic) polymerization including at least one multi-ring alkenyl ethers and one α-fluorinated acrylate. The resulting photoresist compositions exhibit both acceptable resistance to dry etching processing and light transmittance suitable for use with various light sources such as KrF excimer lasers, ArF excimer lasers or F$_2$ excimer lasers, in a photolithography process to produce fine photoresist patterns. In addition to the multi-ring alkenyl ethers and α-fluorinated acrylates, additional monomers comprising one or more cyclic aliphatic and heterocyclic compounds, both unsubstituted and substituted, in particular dihydropyrans, may be incorporated into the photosensitive polymers. Photosensitive polymers can then be produced by combining these various monomer units to form copolymers, terpolymers and higher order polymers, an exemplary embodiment of which may be generally represented by the formula V:

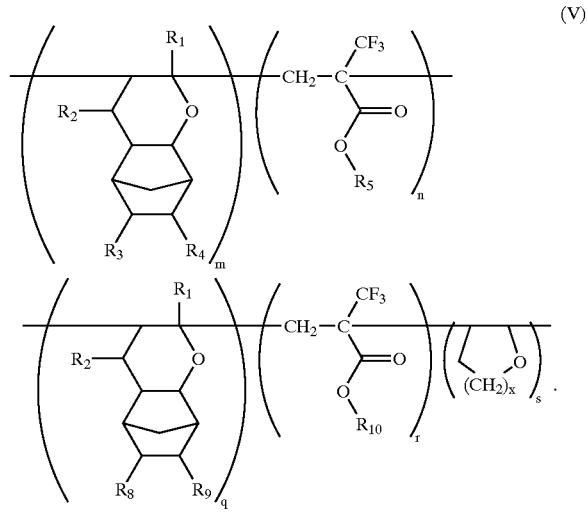

67 Claims, No Drawings

ETHER MONOMERS AND POLYMERS HAVING MULTI-RING STRUCTURES, AND PHOTOSENSITIVE POLYMERS AND RESIST COMPOSITIONS OBTAINED FROM THE SAME

CROSS-REFERENCE TO RELATED APPLICATION

This application is a continuation-in-part and claims domestic priority from U.S. patent application Ser. No. 10/132,804, which was filed Apr. 24, 2002, now U.S. Pat. No. 6,713,228, in the U.S. Patent and Trademark Office, which is, in turn, based on and claims priority from Korean Patent Application No. 2003-85830, which was filed Nov. 28, 2003, in the Korean Intellectual Property Office, the disclosures of which are incorporated herein by reference in their entirety.

BACKGROUND OF THE INVENTION

1. Field of the Invention

The present invention relates to photosensitive polymers, and the production of such polymers, and photoresist compositions that incorporate such polymers that can be used in the production of semiconductor and other microelectronic devices. The photosensitive polymers are prepared by a method of radical (cationic) polymerization from at least two monomers including a multi-ring alkenyl ether and an α-fluorinated acrylate, and may further incorporate one or more cyclic aliphatic and heterocyclic monomers and may be incorporated with one or more solvents, photoacid generators and organic bases to form photoresist compositions.

2. Description of the Related Art

As the manufacture of semiconductor devices becomes complicated and the integration density of semiconductor devices highly increases, there is a need to form a fine pattern. Furthermore, with regard to 1-Gigabit or more semiconductor devices, a pattern size having a design rule of 0.15 µm or less is needed. However, when a conventional photoresist material is exposed with KrF excimer laser (248 nm), there is a limitation in forming such a fine pattern. For this reason, development of a lithography technique using a new exposure light source, ArF excimer laser (193 nm), is under way to be commercially available in the near future. Also, for adoption to the manufacture of semiconductor devices in which formation of patterns of 0.15 µm or less is needed, research into another next-generation technique using $F_2$ excimer laser (157 nm) as a new exposure light source is being extensively conducted.

Whereas research into ArF and $F_2$ excimer laser techniques is being vigorously carried out, existing resist compositions suitable for use in those techniques cause many problems in practical use, compared to conventional KrF resist compositions.

Almost all well-known ArF resist compositions contain (meth)acryl-based polymers. Among these polymers, a methacrylate copolymer having an alicyclic protecting group, which is expressed by the formula below:

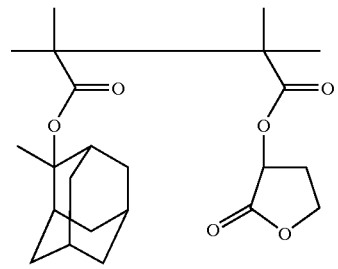

This polymer includes an adamantyl group which tends to enhance the resistance to dry etching, and a lactone group, which tends to increase the adhesiveness, in its methacrylate backbone. As a result, the resolution of the resist and the depth of focus has improved. However, the resistance to dry etching is generally less than satisfactory for fine patterning processes and tends to result in serious line edge roughness in patterns formed from resist layers including such polymers. Another drawback of polymers having the formula above is that the raw materials used to synthesize the polymer is expensive.

As another conventional resist composition, a cycloolefin-maleic anhydride (COMA) alternating polymer having the following formula has been suggested:

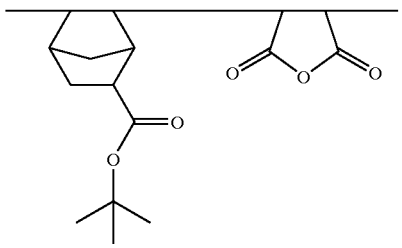

In the production of copolymer, such as a COMA alternating polymer having the formula above, resistance to dry etching is improved and the production cost of raw material is cheap, whereas resolution of the polymer sharply decreases. Also, the copolymer has a glass transition temperature ($T_g$) of 200° C. or higher due to the structural strength of norbornene contained in the backbone, resulting in processing difficulty. In addition, the synthetic polymers have in their backbone the alicyclic group, which shows prominent hydrophobicity, and thus the adhesiveness to neighboring material layers is very poor.

To overcome the described problems, in recent years, polymers having various structures have been proposed, the polymers exemplified by a copolymer of a COMA system and a monomer units having a (meth)acylate-based backbone:

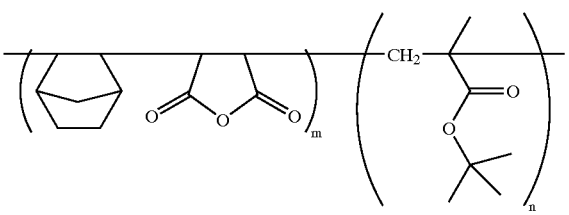

Since the copolymer having the above structure has a glass transition temperature ($T_g$) lower than that of the COMA system, the processing can be easily carried out. Also, since a polarity change occurs to (meth)acrylate monomer units, increased resolution can be achieved. However, according to reports hitherto made, resistance to dry etching has not been enhanced very much. To increase the resistance to dry etching, a bulky protecting group such as an adamantly group, rather than a t-butyl group, is introduced to the above structure. However, the resulting resist still exhibits weak resistance to dry etching or poor patterns.

As the pattern rule becomes finer in the manufacture of semiconductor devices, the aspect ratio is considerably increased, resulting in the collapse of patterns. To avoid this, a lithography technique using ArF excimer lasers may be used. However, in the case of using the lithography technique using ArF excimer lasers, patterns must be formed such that a resist layer is coated on a wafer to a thickness of 4000 Å or less. As the thickness of the resist layer is reduced as above, it is necessary to enhance resistance to dry etching.

Another conventional resist composition proposed for enhancing resistance to dry etching includes a polymer having only a norbornene structure in its backbone, represented by the following formula:

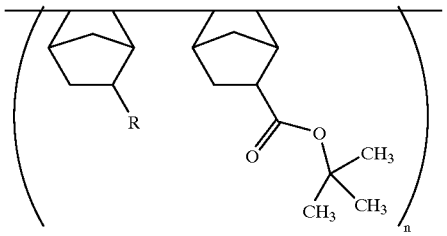

Photoresists incorporating such polymers, however, tend to be hydrophobic, suffer from reduced adhesion and exhibit reduced transmittance, reducing their utility for forming fine patterns. Further, in order to obtain the above structure, a catalyst including a heavy metal such as platinum or nickel is necessary to induce the desired polymerization. However, a portion of the heavy metal catalyst remains in the resulting polymer product even after purification. As a result, photoresist compositions incorporating such polymers present a serious risk of heavy metal contamination and would not be practical for use in most semiconductor process applications.

Other conventional photoresists have included copolymers of norborene and tetrafluoroethylene as represented by the formula:

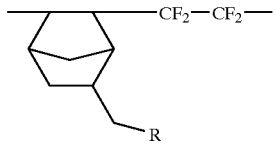

that tend to exhibit improved transmittance as a result of the additional fluorine in the main chain, but also tend to have poor adhesion characteristics. Other photoresists have incorporated more highly fluorinated polymers that may be represented by the formulas:

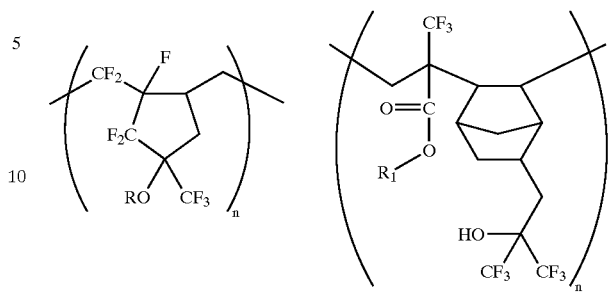

to provide additional improvements in transmittance, but these improvements tend to come at the expense of reduced resistance to dry etch processes and/or reduced adhesion.

SUMMARY OF THE INVENTION

Exemplary embodiments of the present invention provide monomers including multi-ring alkenyl ethers and α-fluorinated acrylates, and methods for producing such monomers, that may be used as raw materials for producing improved photosensitive polymers that can be adapted for use with various light sources, particularly light sources having shorter wavelengths such as KrF excimer lasers, ArF excimer lasers and $F_2$ excimer lasers, in a photolithography process.

Exemplary embodiments of the present invention provide methods for producing improved photosensitive polymers utilizing a simplified synthesis method to form polymers including at least one multi-ring alkenyl ether and one α-fluorinated acrylate that can provide satisfactory resistance to dry etching processes while being substantially free of contamination resulting from the use of a heavy metal catalyst during the polymerization.

Exemplary embodiments of the present invention provide improved resist compositions including polymers of multi-ring alkenyl ether and α-fluorinated acrylate monomers that exhibit both acceptable resistance to dry etching processing and light transmittance suitable for use with various light sources such as KrF excimer lasers, ArF excimer lasers or $F_2$ excimer lasers, in a photolithography process to produce fine photoresist patterns.

The multi-ring alkenyl ethers monomers suitable for use in the present invention may be generally represented by the formula (I):

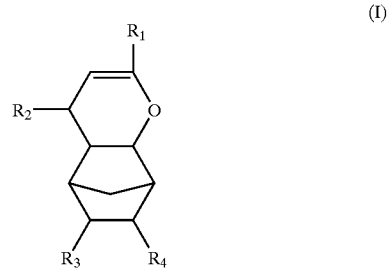

(I)

wherein $R_1$ and $R_2$ are independently selected from hydrogen and methyl, $R_3$ and $R_4$ are independently selected from a group consisting of hydrogen, hydroxy, alkyl, cycloalkyl, haloalkyl, alkoxy, carboxyl, carbonyl, ester and acid labile groups having 1–20 carbon atoms.

Exemplary monomers according to formula I include monomers that may be generally represented by the following formulas:

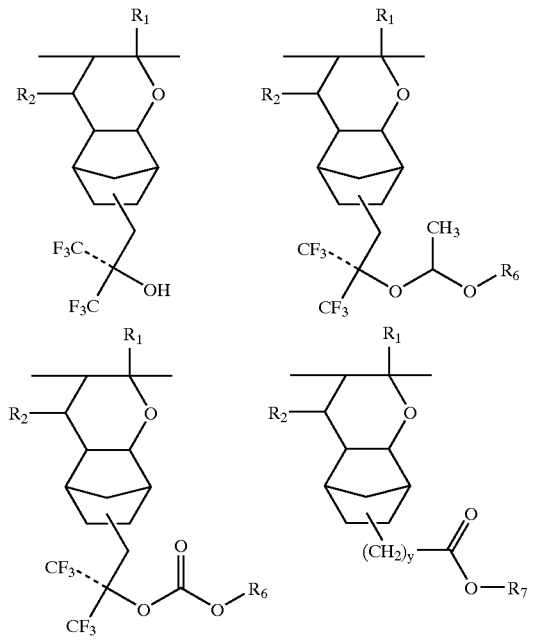

wherein $R_1$ and $R_2$ are independently selected from hydrogen and methyl; $R_6$ is selected from alkyls and substituted alkyls having at least one and no more than 20 carbon atoms; y is 0, 1 or 2; and $R_7$ is an acid labile group including a hydrocarbon or a substituted hydrocarbon having at least 4 and no more than 20 carbons.

The α-fluorinated acrylate monomers suitable for use in the present invention may be generally represented by the formula (II):

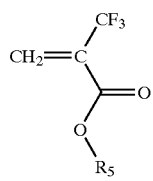

(II)

wherein $R_5$ is typically selected from a group consisting of hydrogen, hydroxy, substituted and unsubstituted alkyls, substituted and unsubstituted cycloalkyls, substituted and unsubstituted alkoxys and acid labile groups having 1–20 carbon atoms.

Exemplary monomers according to formula II include monomers that may be generally represented by the following formulas:

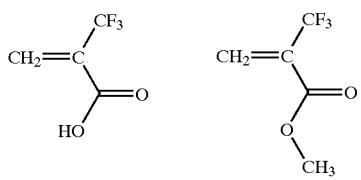

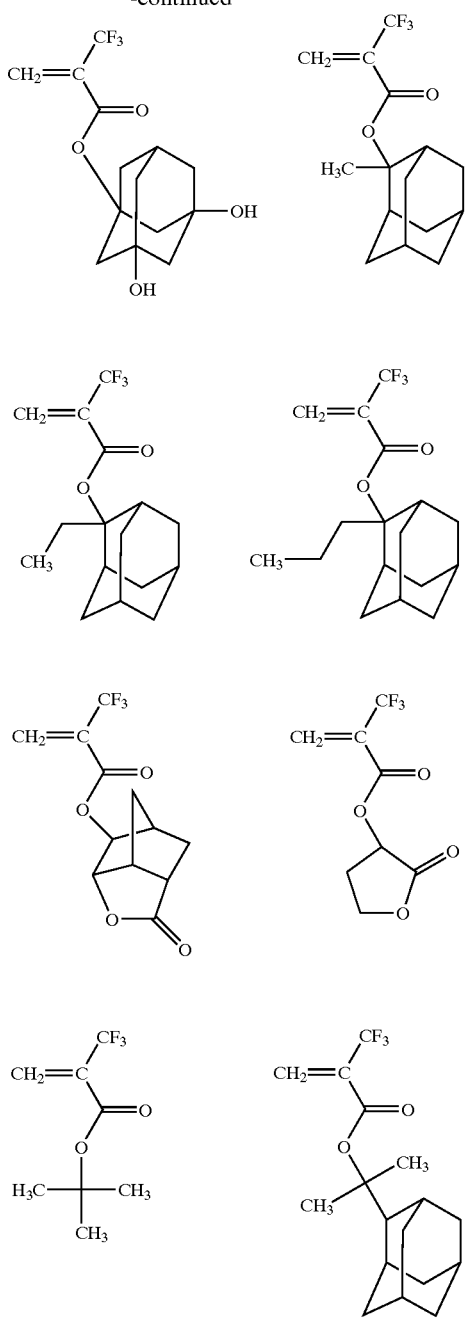

In addition to the multi-ring alkenyl ethers and α-fluorinated acrylates, additional monomors comprising one or more cyclic aliphatic and heterocyclic compounds, both unsubstituted and substituted, may be incorporated into the photosensitive polymers. In particular, dihydropyrans, that may be generally represented by the formula:

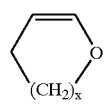

in which x is preferably 1 or 2, may be incorporated into the photosensitive polymer.

Photosensitive polymers can then be produced by combining these various monomer units to form copolymers, terpolymers, tetrapolymers and even higher order polymers, exemplary embodiments of which may be generally represented by the formulas:
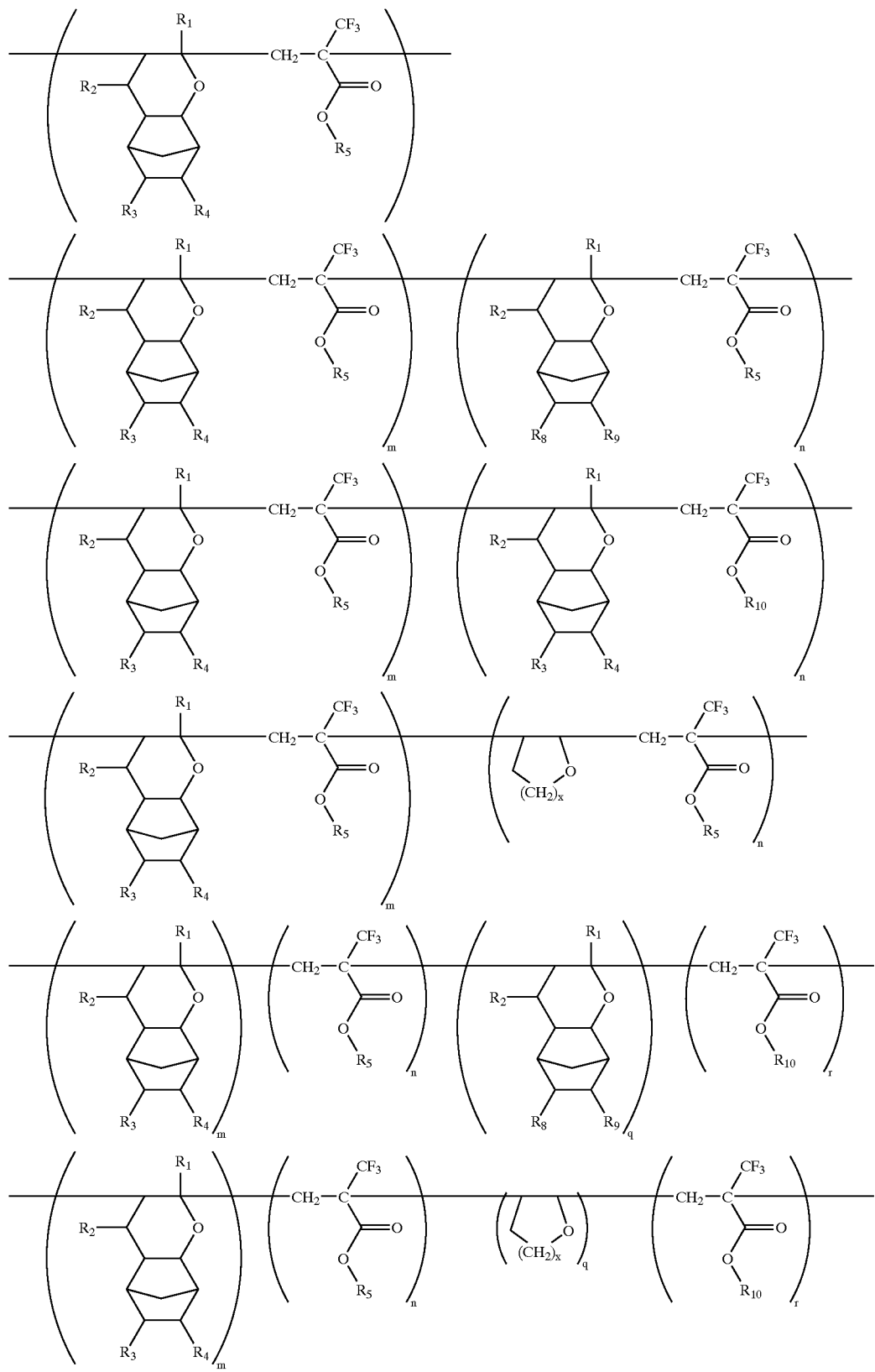

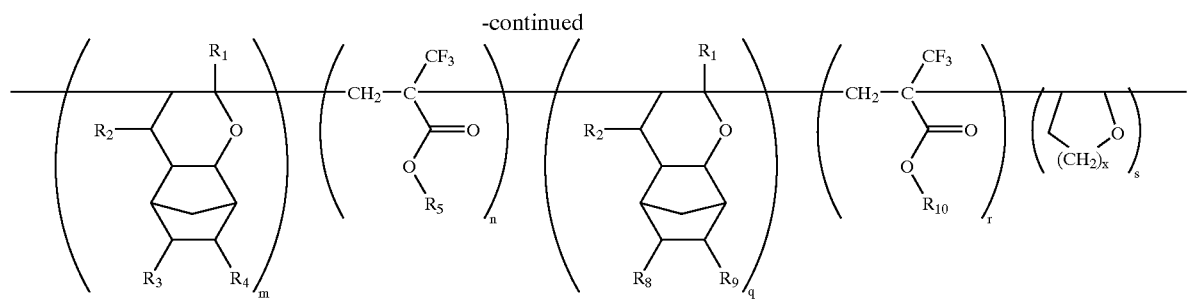

wherein $R_1$ and $R_2$ are independently selected from hydrogen and methyl; $R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups having 1–20 carbon atoms, both substituted and unsubstituted; $R_5$ and $R_{10}$ are independently selected from a group consisting of hydrogen, hydroxy, substituted and unsubstituted alkyls, substituted and unsubstituted cycloalkyls, substituted and unsubstituted alkoxys and acid labile groups having 1–20 carbon atoms; x is 1 or 2; and m, n, q, r and s are the mole fractions of the various monomers or monomer pairs present in the polymer.

In particular, one or more of $R_3$, $R_4$, $R_8$ and $R_9$ may comprise a group generally represented by the formula:

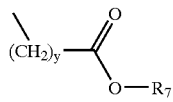

wherein $R_7$ is an alkyl group having 4–12 carbon atoms and y is 0, 1 or 2, preferably 1 or 2. More preferably, $R_7$ is selected from a group consisting of t-butyl, tetrahydropyranyl, and a substituted or unsubstituted alicyclic hydrocarbon having 6–12 carbon atoms, including, for example, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl group, 1-adamantyl-1-methylethyl, 2-methyl-2-fenchyl and 2-ethyl-2-fenchyl groups.

Exemplary photoresist compositions according to the invention will incorporate photosensitive polymer or polymers having various structures as defined above and will preferably have weight average molecular weights within a range of about 3,000–100,000. Exemplary photoresist compositions according to the invention will also typically incorporate one or more photoacid generators (PAG), with the amount of the PAG included in the photoresist composition being 1–30 wt % on the basis of the weight of the photosensitive polymer. Preferably, the PAG includes triarylsulfonium salts, diaryliodonium salts, sulfonates, or mixtures thereof. More preferably, the PAG is selected from triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, PFOS (triphenylsulfonium perfluorooctanesulfonate), diphenyliodonium PFOS, methoxydiphenyliodonium PFOS, di-t-butyldiphenyliodonium triflate, N-hydroxysuccinimide PFOS, norbornene-dicarboximide PFOS, and mixtures thereof.

Exemplary photoresist compositions according to the above described aspects of the present invention will also typically include an organic base with the amount of the organic base typically being 0.01–2.0 wt % on the basis of the weight of the photosensitive polymer. Preferably, the organic base includes a tertiary amine compound alone or a mixture of at least two tertiary amine compounds. Examples of suitable organic bases include triethylamine, triisobutylamine, triisooctylamine, triisodecylamine, diethanolamine, triethanolamine, N-alkyl substituted pyrrolidinone, N-alkyl substituted caprolactam, N-alkyl substituted valerolactam and mixtures thereof. The resist composition according to the above described aspects of the present invention may further include one or more surfactants, typically within a range from about 30 to 200 ppm.

The photosensitive polymer according to the present invention has a structure that has improved resistance to dry etching and good adhesiveness to underlying layers. Also, since the photosensitive polymer according to the present invention can be obtained through radical (cationic) polymerization, a multi-ring backbone structure can be provided without contamination due to a heavy metal catalyst. Further, the photosensitive polymer included in a resist composition according to the present invention can be adopted to various light sources including KrF excimer lasers (248 nm), ArF excimer lasers (193 nm) or F2 excimer lasers (157 nm). In particular, the resist composition obtained from the photosensitive polymer according to the present invention exhibits improved transmittance at 157 nm. The resist compositions incorporating the photosensitive polymers according to the present invention provide improved resistance to dry etching and good transmittance, thereby supporting lithographic processes capable of achieving high resolution.

DETAILED DESCRIPTION OF THE INVENTION

As noted above, a variety of monomers may be utilized for producing the photosensitive polymers and photoresist compositions of the present invention. Provided below are a series of examples illustrating the synthesis of certain exemplary monomers useful in the present invention. Those of ordinary skill in the art will appreciate that these examples are illustrative only and do not attempt to illustrate each of the acceptable monomers.

MONOMER SYNTHESIS EXAMPLES

Monomer Synthesis Example 1-1

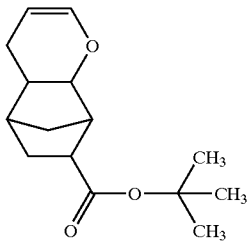

An autoclave was charged with a solution containing a mixture of t-butyl 5-norbornene-2-carboxylate (233 g: 1.2 mol), acrolein (22.4 g: 0.4 mol) and hydroquinone (0.5 g) as an internal standard. The autoclave was then purged with $N_2$ and sealed. The solution was then heated to a reaction temperature of 170° C. and agitated under a pressure of 20 atm for a reaction period of about 15 hours to produce a product solution containing t-butyl 3-oxa-tricyclo[6.2.1.0$^{2,7}$]undec-4-ene-10-carboxylate. The product solution was then cooled and depressurized, after which it was distilled to separate the t-butyl 3-oxa-tricyclo[6.2.1.0$^{2,7}$]undec-4-ene-10-carboxylate monomer product. The synthesis provided a 45% yield of the monomer product based on the original acrolein charge, thus illustrating the utility of this synthesis for producing cyclic alkenyl ethers according to the present invention.

Monomer Synthesis Example 1-2

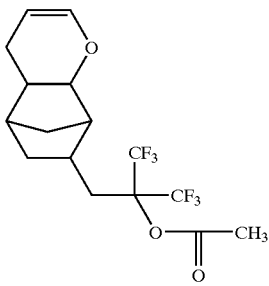

An autoclave was charged with 3-(5-bicyclo[2.2.1]hepten-2-yl)-1,1,1-trifluoro-2-(tifluoromethyl)-2-propyl acetate (284 g) and acrolein (16.8 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 3-(3-oxa-tricyclo[6.2.1.0$^{2,7}$]undec-4-en-10-yl)-1,1,1-trifluoro-2-(trfluoromethyl)-2-propyl acetate. The product solution was then cooled and depressurized, after which it was distilled to separate the 3-(3-oxa-tricyclo[6.2.1.0$^{2,7}$]undec-4-en-10-yl)-1,1,1-trifluoro-2-(trfluoromethyl)-2-propyl acetate monomer product from the product solution. The synthesis provided a 85% yield of the monomer product based on the original acrolein charge, thus illustrating the utility of this synthesis for producing cyclic alkenyl ethers according to the present invention.

Monomer Synthesis Example 1-3

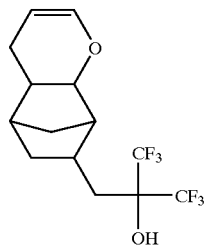

An autoclave was charged with 2-bicyclo[2.2.1]hept-5-en-2-ylmethyl-1,1,1,3,3,3-hexafluoro-propan-2-ol (328 g) and acrolein (22.4 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 1,1,1,3,3,3-hexafluoro-2-(3-oxa-tricyclo[6.2.1.0$^{2,7}$]undec-4-en-10-ylmethyl)-propan-2-ol. The product solution was then cooled and depressurized, after which it was distilled to separate the 1,1,1,3,3,3-hexafluoro-2-(3-oxa-tricyclo[6.2.1.0$^{2,7}$]undec-4-en-10-ylmethyl)-propan-2-ol monomer product (66 g) from the product solution.

Monomer Synthesis Example 1-4

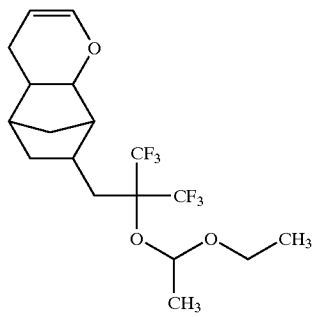

An autoclave was charged with 5-[2-(1-ethoxy-ethoxy)-3,3,3-trifluoro-2-trifluoromethyl-propyl]-bicyclo[2.2.1]hept-2-ene (415 g) and acrolein (22.4 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 10-[2-(1-ethoxy-ethoxy)-3,3,3-trifluoro-2-trifluoromethyl-propyl]-3-oxa-tricyclo[6.2.1.0$^{2,7}$]undec-4-ene. The product solution was then cooled and depressurized, after which it was distilled to separate the 10-[2-(1-ethoxy-ethoxy)-3,3,3-trifluoro-2-trifluoromethyl-propyl]-3-oxa-tricyclo[6.2.1.0$^{2,7}$]undec-4-ene monomer product (78 g) from the product solution.

Monomer Synthesis Example 1-5

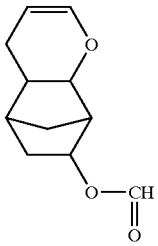

An autoclave was charged with 5-norborne-2-yl formate (248 g) and acrolein (33.6 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 3-oxa-tricyclo[6.2.1.0$^{2,7}$]undec-4-en-10-yl formate. The product solution was then cooled and depressurized, after which it was distilled to separate the 3-oxa-tricyclo[6.2.1.0$^{2,7}$]undec-4-en-10-yl formate monomer product (57 g) from the product solution.

Monomer Synthesis Example 1-6

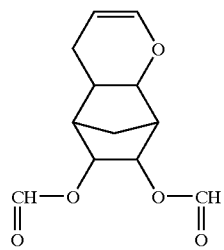

An autoclave was charged with 5-norbornene-2,3-yl diformate (218 g) and acrolein (22.4 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 3-oxa-tricyclo[6.2.1.0$^{2,7}$]undec-4-en-9,10-yl diformate. The product solution was then cooled and depressurized, after which it was distilled to separate the 3-oxa-tricyclo[6.2.1.0$^{2,7}$]undec-4-en-9,10-yl diformate monomer product (47 g) from the product solution.

Monomer Synthesis Example 1-7

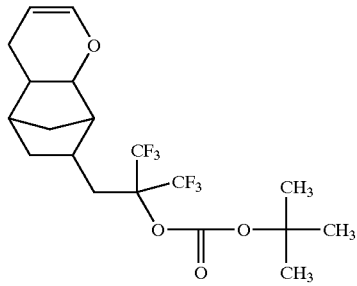

An autoclave was charged with 1-bicyclo[2.2.1]hept-5-en-2-ylmethyl-2,2,2-trifluoro-1-trifluoromethyl-ethyl tert-butyl carbonate (284 g) and acrolein (16.8 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 2,2,2-trifluoro-1-(3-oxa-tricyclo [6.2.1.0$^{2,7}$]undec-4-en-10-ylmethyl)-1-trifluoromethyl-ethyl tert-butyl carbonate. The product solution was then cooled and depressurized, after which it was distilled to separate the 2,2,2-trifluoro-1-(3-oxa-tricyclo[6.2.1.0$^{2,7}$]undec-4-en-10-ylmethyl)-1-trifluoromethyl-ethyl tert-butyl carbonate monomer product (56 g) from the product solution.

Monomer Synthesis Example 1-8

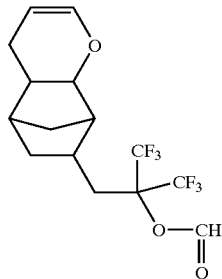

An autoclave was charged with 3-(5-bicyclo[2.2.1] hepten-2-yl)-1,1,1-trifluoro-2-(trifluoromethyl)-2-ethyl formate (284 g) and acrolein (16.8 g) as an internal standard. The autoclave was then purged with $N_2$ and sealed. The solution was then heated to a reaction temperature of 170° C. and agitated under a pressure of 20 atm for a reaction period of about 15 hours to produce a product solution containing 3-(3-oxa-tricyclo[6.2.1.0$^{2,7}$]undec-4-en-10-yl)-1, 1,1-trifluoro-2-(trifluoromethyl)-2-ethyl formate. The product solution was then cooled and depressurized, after which it was distilled to separate the 3-(3-oxa-tricyclo[6.2.1.0$^{2,7}$] undec-4-en-10-yl)-1,1,1-trifluoro-2-(trifluoromethyl)-2-ethyl formate monomer product (56 g) from the product solution.

As noted above, a variety of monomers may be utilized for producing the photosensitive polymers and photoresist compositions of the present invention. Provided below are a series of examples illustrating the synthesis of certain exemplary polymers according to the present invention. Those of ordinary skill in the art will appreciate that these examples are illustrative only and do not attempt to illustrate each of the acceptable polymers.

POLYMER SYNTHESIS EXAMPLES

Copolymer Synthesis Example 2-1

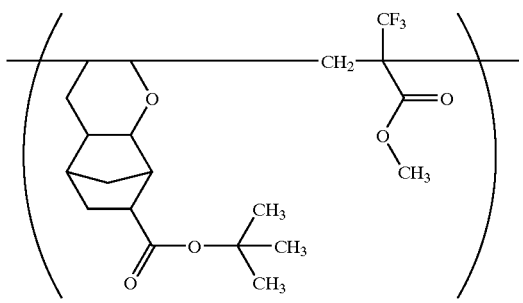

T-butyl 3-oxa-tricyclo[6.2.1.0$^{2,7}$]undec-4-ene-10-carboxylate (25 g), prepared according to Monomer Synthesis Example 1-1, and 2-trifluoromethylacrylate (15.0 g) were dissolved in tetrahydrofuran (THF) (100 g) and placed in a reactor, in this instance a 3-neck round-bottom flask, after which the reactor was purged with $N_2$ gas. After adding 2,2'-azobisisobutyronitrile (AIBN) (2 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 75% and produced a copolymer having Mw=9,800 and a polydispersity (Mw/Mn) of 1.9.

Copolymer Synthesis Example 2-2

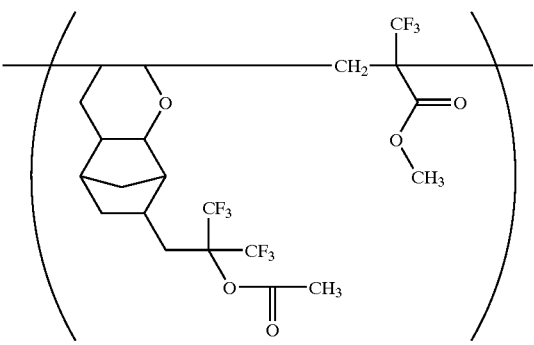

Alkenyl ether (37.2 g), prepared according to Monomer Synthesis Example 1-2, and 2-trifluoromethylacrylate (15.0 g) were dissolved in THF (100 g) and placed in a reactor, after which the reactor was purged with $N_2$ gas. After adding AIBN (1 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 73% and produced a copolymer having Mw=13,000 and a polydispersity (Mw/Mn) of 2.1.

Copolymer Synthesis Example 2-3

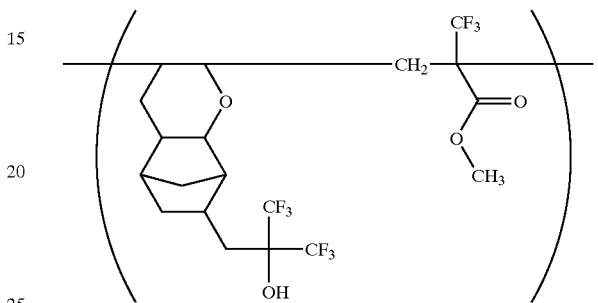

The copolymer prepared according to Copolymer Synthesis Example 2-2 was dissolved in a mixture of THF and methanol (1:1, 100 ml) to form a solution. An ammonia solution (28%, 5.0 g) was then added to the solution to form a reaction solution. The reaction solution was refluxed for 5 hours to form a product solution, after which the product solution was cooled to room temperature and was neutralized (pH=7) through the drop wise addition of an acid solution (HCl, 10%). The product solution was then precipitated slowly in excessive water (×10) and filtered to separate the precipitates. The first retentate was then dissolved in THF and re-precipitated in methanol solution. The precipitated solution was filtered and the second retentate was dried in a vacuum oven maintained at 50° C. for about 24 hours to obtain a modified polymer product. This synthesis exhibited a yield of about 88% and produced a copolymer having Mw=12,700 and a polydispersity (Mw/Mn) of 2.0.

Copolymer Synthesis Example 2-4

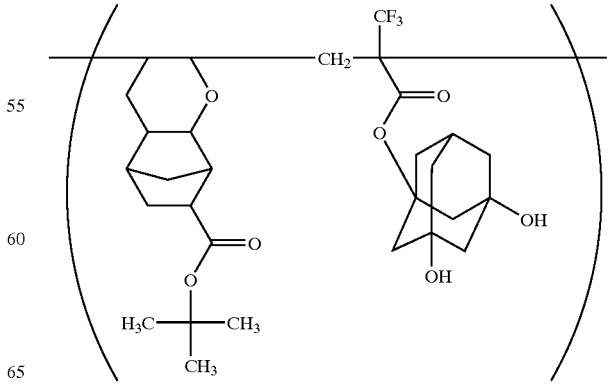

3-oxa-tricyclo[6.2.1.0$^{2,7}$]undec-4-ene-10-yl carboxylate (12.5 g), prepared according to Monomer Synthesis Example 1-1, and α-trifluoromethyl-3,5-dihydroxy-adamantane-1-yl acetate (15.3 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 95% and produced a copolymer having Mw=9,100 and a polydispersity (Mw/Mn) of 2.3.

Copolymer Synthesis Example 2-5

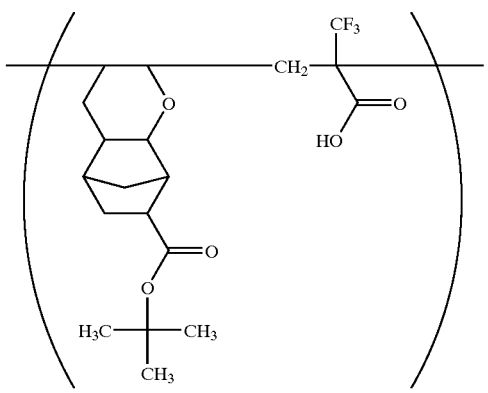

3-oxa-tricyclo[6.2.1.0$^{2,7}$]undec-4-ene-10-yl carboxylate (12.5 g), prepared according to Monomer Synthesis Example 1-1, and 2-trifluoromethyl acrylic acid (7 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 92% and produced a copolymer having Mw=15,000 and a polydispersity (Mw/Mn) of 2.4.

Copolymer Synthesis Example 2-6

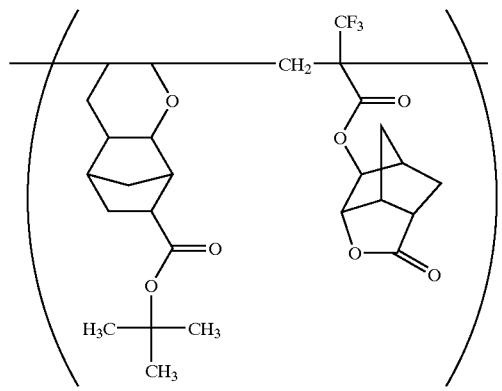

3-oxa-tricyclo[6.2.1.0$^{2,7}$]undec-4-ene-10-yl carboxylate (12.5 g), prepared according to Monomer Synthesis Example 1-1, and α-trifluoromethyl-5-oxo-4-oxa-tricyclo[4.2.1.0$^{3,7}$]non-2-yl acrylate (13.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 91% and produced a copolymer having Mw=9,300 and a polydispersity (Mw/Mn) of 2.3.

Copolymer Synthesis Example 2-7

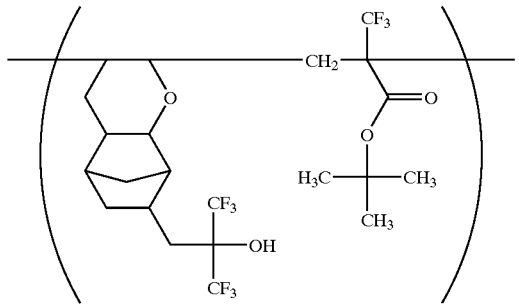

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3, and 2-trifluoromethyl t-butylacrylate (9.8 g) were dissolved in THF (100 g) and placed in a reactor, after which the reactor was purged with $N_2$ gas. After adding AIBN (1 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 96% and produced a copolymer having Mw=21,000 and a polydispersity (Mw/Mn) of 2.1.

Copolymer Synthesis Example 2-8

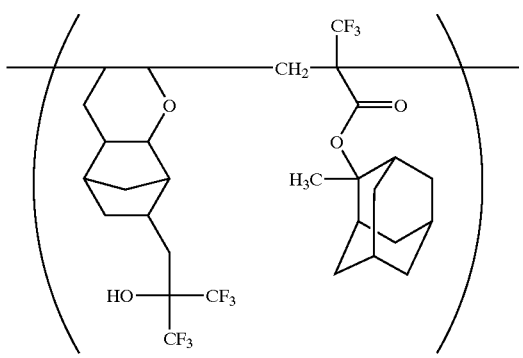

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3, and α-trifluoromethyl-2-methyl-adamantane-2-yl acrylate (14.4 g) were dissolved in THF (100 g) and placed in a reactor, after which the reactor was purged with $N_2$ gas. After adding AIBN (1 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 93% and produced a copolymer having Mw=15,800 and a polydispersity (Mw/Mn) of 2.2.

Copolymer Synthesis Example 2-9

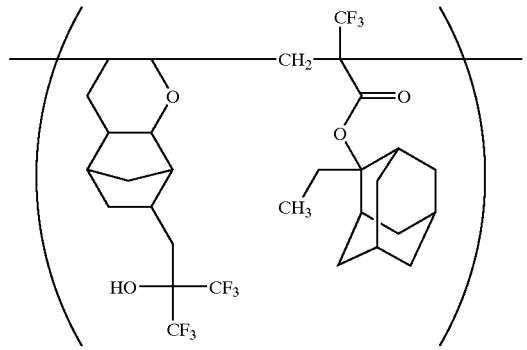

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3, and α-trifluoromethyl-2-ethyl-adamantane-2-yl acrylate (15.1 g) were dissolved in THF (100 g) and placed in a reactor, after which the reactor was purged with $N_2$ gas. After adding AIBN (2 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 91% and produced a copolymer having Mw=13,900 and a polydispersity (Mw/Mn) of 1.8.

Copolymer Synthesis Example 2-10

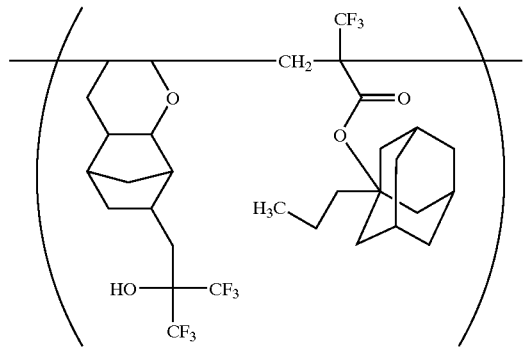

1,1,1,3,3,3-hexafluoro-2-(3-oxa-tricyclo[6.2.1.0$^{2,7}$]undec-4-ene-10-ylmethyl)propan-2-ol (16.5 g), prepared according to Monomer Synthesis Example 1-3, and α-trifluoromethyl-2-propyl-adamantane-2-yl acrylate (15.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 93% and produced a copolymer having Mw=17,200 and a polydispersity (Mw/Mn) of 2.1.

Copolymer Synthesis Example 2-11

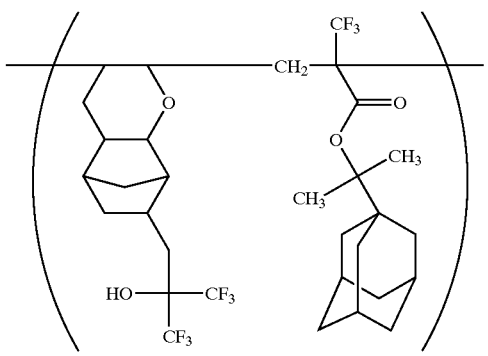

1,1,1,3,3,3-hexafluoro-2-(3-oxa-tricyclo[6.2.1.0$^{2,7}$]undec-4-ene-10-ylmethyl)propan-2-ol (16.5 g), prepared according to Monomer Synthesis Example 1-3, and α-trifluoromethyl-1-adamantane-1-yl-1-methyl-ethyl acrylate (15.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 93% and produced a copolymer having Mw=15,500 and a polydispersity (Mw/Mn) of 1.9.

Copolymer Synthesis Example 2-12

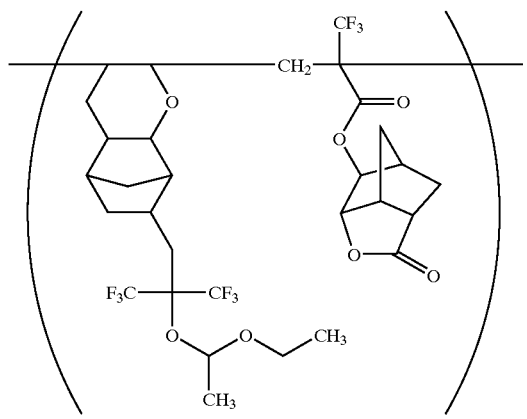

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, and α-trifluoromethyl-5-oxo-4-oxa-tricyclo[4.2.1.0$^{3,7}$]non-2-yl acrylate (13.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 89% and produced a copolymer having Mw=17,700 and a polydispersity (Mw/Mn) of 2.2.

Copolymer Synthesis Example 2-13

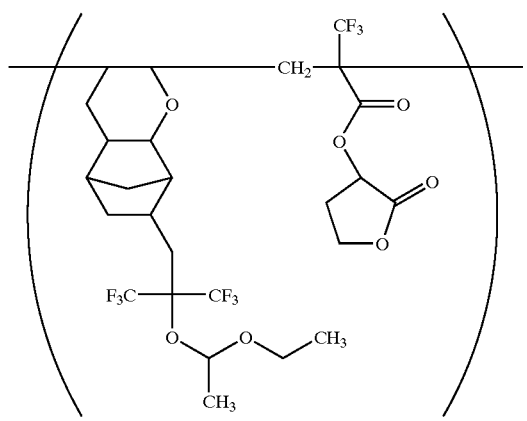

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, and α-trifluoro-2-oxo-tetrahydro-furan-3-yl ester (11.2 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 88% and produced a copolymer having Mw=19,100 and a polydispersity (Mw/Mn) of 1.9.

ene (20.1 g), prepared according to Monomer Synthesis Example 1-4, and α-trifluoromethyl-3,5-dihydroxy-adamantane-1-yl acrylate (15.3 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the copolymer product. This synthesis exhibited a yield of about 84% and produced a copolymer having Mw=22,700 and a polydispersity (Mw/Mn) of 2.0.

Terpolymer Synthesis Example 3-1

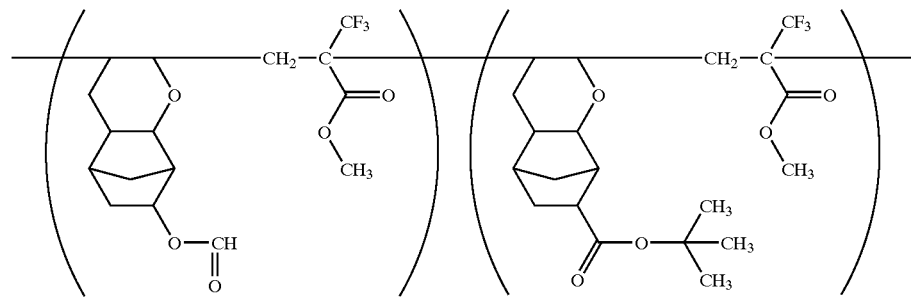

Copolymer Synthesis Example 2-14

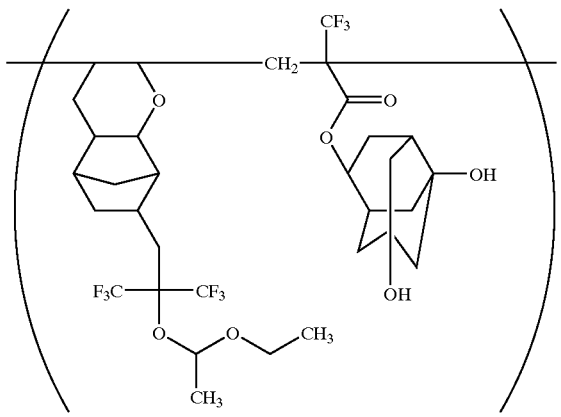

10-[2-(1-ethoxy-ethoxy)-3,3,3-trifluoro-2-trifluoromethyl-propyl]-3-oxa-tricyclo[6.2.1.0$^{2,7}$]undec-4-

T-butyl 3-oxa-tricyclo[6.2.1.0$^{2,7}$]undec-4-ene-10-carboxylate (12.5 g), prepared according to Monomer Synthesis Example 1-1, 3-oxa-tricyclo[6.2.1.0$^{2,7}$]undec-4-ene-10-yl formate (9.7 g), prepared according to Monomer Synthesis Example 1-5, and 2-trifluoromethyl acrylate (15.4 g) were dissolved in THF (100 g) and placed in a reactor, after which the reactor was purged with N$_2$ gas. After adding AIBN (2 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 70% and produced a terpolymer having Mw=11,000 and a polydispersity (Mw/Mn) of 2.1.

Terpolymer Synthesis Example 3-2

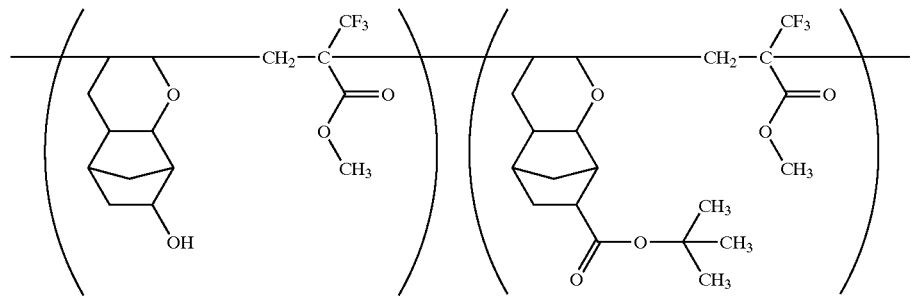

The terpolymer prepared according to Terpolymer Synthesis Example 3-1 was dissolved in a mixture of THF and methanol (1:1, 100 ml) to form a solution. An ammonia solution (28%, 5.0 g) was then added to the solution to form a reaction solution. The reaction solution was refluxed for 5 hours to form a product solution, after which the product solution was cooled to room temperature and was neutralized (pH=7) through the drop wise addition of an acid solution (HCl, 10%). The product solution was then precipitated slowly in excessive water (X10) and filtered to separate the precipitates. The first retentate was then dissolved in THF and re-precipitated in methanol solution. The precipitated solution was filtered and the second retentate was dried in a vacuum oven maintained at 50° C. for about 24 hours to obtain a modified polymer product. This synthesis exhibited a yield of about 85% and produced a terpolymer having Mw=10,500 and a polydispersity (Mw/Mn) of 1.95.

Terpolymer Synthesis Example 3-3

T-butyl 3-oxa-tricyclo[6.2.1.0$^{2,7}$]undec-4-ene-10-carboxylate (12.5 g), prepared according to Monomer Synthesis Example 1-1, 3-oxa-tricyclo[6.2.1.0$^{2,7}$]undec-4-ene-9,10-yl diformate (11.9 g), prepared according to Monomer Synthesis Example 1-6, and 2-trifluoromethyl acrylate (15.4 g) were dissolved in THF (100 g) and placed in a reactor, after which the reactor was purged with N$_2$ gas. After adding AIBN (3 mol %) to the reactor, the polymerization proceeded for a polymerization time of about 12 hours at a polymerization temperature of about 70° C. under N$_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 67% and produced a terpolymer having Mw=10,000 and a polydispersity (Mw/Mn) of 1.8.

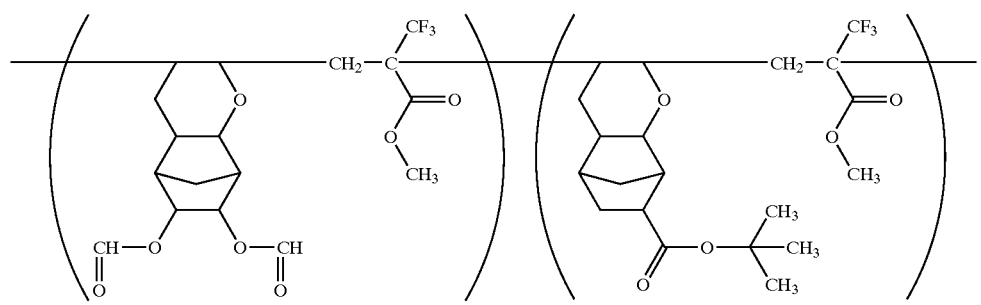

Terpolymer Synthesis Example 3-4

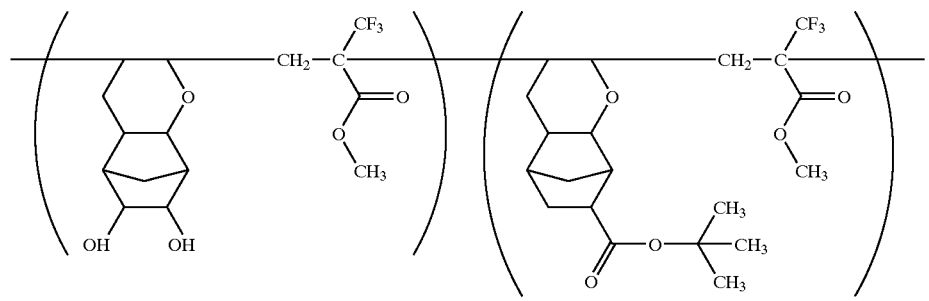

The terpolymer prepared according to Terpolymer Synthesis Example 3-2 was dissolved in a mixture of THF and methanol (1:1, 100 ml) to form a solution. An ammonia solution (28%, 5.0 g) was then added to the solution to form a reaction solution. The reaction solution was refluxed for 5 hours to form a product solution, after which the product solution was cooled to room temperature and was neutralized (pH=7) through the drop wise addition of an acid solution (HCl, 10%). The product solution was then precipitated slowly in excessive water (X10) and filtered to separate the precipitates. The first retentate was then dissolved in THF and re-precipitated in methanol solution. The precipitated solution was filtered and the second retentate was dried in a vacuum oven maintained at 50° C. for about 24 hours to obtain a modified polymer product. This synthesis exhibited a yield of about 92% and produced a terpolymer having Mw=9,900 and a polydispersity (Mw/Mn) of 1.79.

Terpolymer Synthesis Example 3-5

The copolymer (10.0 g) prepared according to Copolymer Synthesis Example 2-3 was dissolved in a dichloromethane solution and then purged with $N_2$ gas. Ethyl vinyl ether (5.0 g) and toluene sulfonic acid (0.5 g) were added to the solution, which was then allowed to react for a reaction time of about 3 hours at room temperature (about 25° C.) to form a product solution. The product solution was then precipitated slowly in excessive water and filtered to separate the precipitates. The first retentate was then dissolved in THF, re-precipitated in a methanol solution and then filtered to separate the precipitates. The second retentate was then dried in a vacuum oven maintained at 50° C. for about 24 hours to obtain the modified terpolymer product. This synthesis produced a terpolymer having Mw=14,100 and a polydispersity (Mw/Mn) of 2.2.

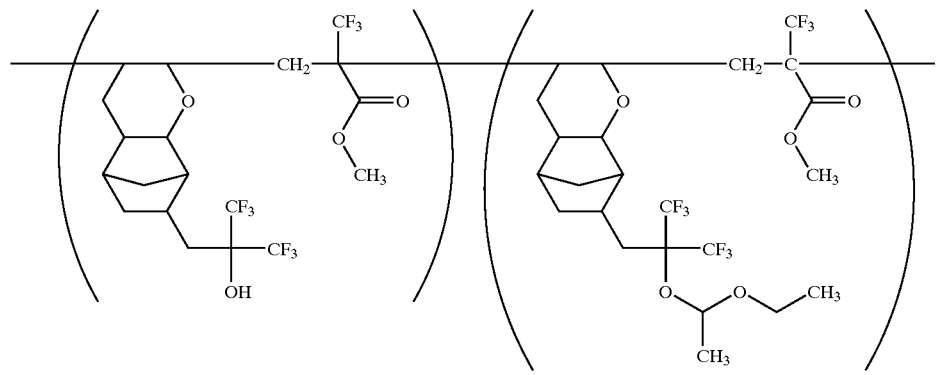

Terpolymer Synthesis Example 3-6

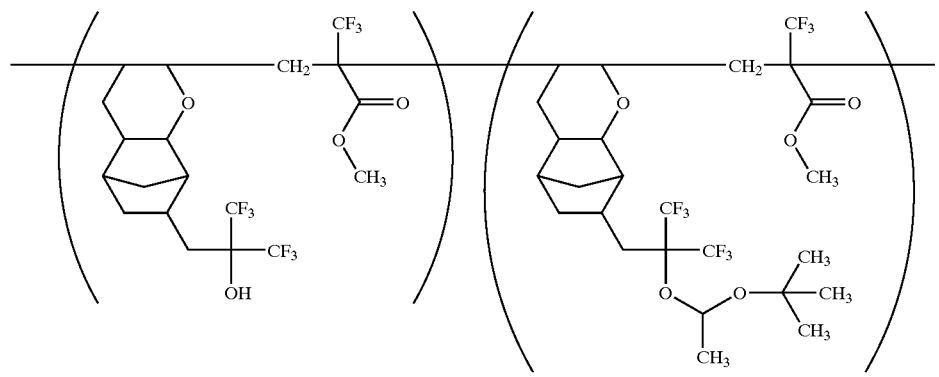

A solution was prepared by dissolving sodium hydride (0.61 g, 60% dispersed in mineral oil) in THF (60 ml) and cooled to about 0° C. to form a hydride solution. The copolymer (10.0 g) prepared according to Copolymer Synthesis Example 2-3 was dissolved in THF (50 ml) and slowly added to the hydride solution. A solution of di-t-butyl dicarbonate (2.8 g) in THF (20 ml) was also added to the hydride solution to form a reaction solution. The reaction solution was allowed to reach room temperature and then agitated for a reaction period of about 24 to obtain a product solution. After the reaction period had been completed, the unreacted sodium hydride was quenched by putting ice in the product solution. A portion of the product solution solvent was then volatilized to reduce the volume of the product solution to approximately 50 ml. The concentrated product solution was then precipitated slowly in excessive water and filtered to separate the precipitates. The first retentate was then dissolved in THF, re-precipitated with water and then filtered to separate the precipitates. The second retentate was then dried in a vacuum oven maintained at 50° C. for about 24 hours to obtain the modified terpolymer product. This synthesis produced a terpolymer having Mw=14,300 and a polydispersity (Mw/Mn) of 2.2.

Terpolymer Synthesis Example 3-7

T-butyl 3-oxa-tricyclo[6.2.1.0$^{2,7}$]undec-4-ene-10-carboxylate (13 g), prepared according to Monomer Synthesis Example 1-1,3-(3-oxa-tricyclo[6.2.1.0$^{2,7}$]undec-4-ene-10-yl)-1,1,1-trifluoro-2-(trifluoromethyl)-2-prophyl acetate (18 g), prepared according to Monomer Synthesis Example 1-2, and 2-trifluoromethylacrylic acid (14 g) were dissolved in THF (200 ml) and placed in a reactor, after which the reactor was purged with $N_2$ gas. After adding AIBN (1 mol %) to the reactor, the polymerization proceeded for a polymerization time of about 12 hours at a polymerization temperature of about 70° C. under $N_2$ purging to obtain a product solution. After terminating the polymerization, the reaction product was precipitated from the product solution slowly in excessive hexane and filtered to separate the precipitates. This first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 73% and produced a terpolymer having Mw=12,000 and a polydispersity (Mw/Mn) of 2.1.

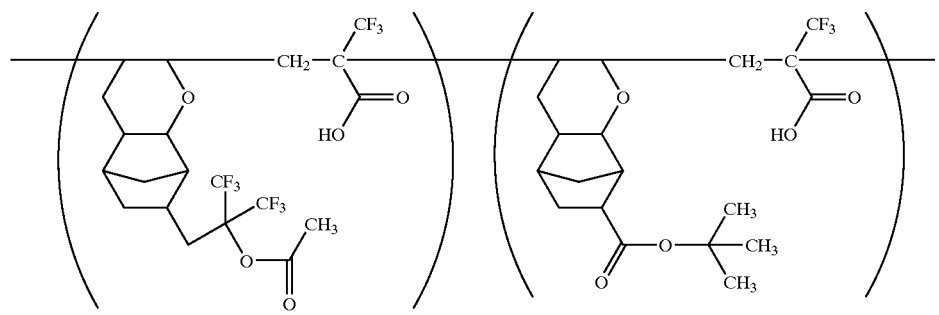

Terpolymer Synthesis Example 3-8

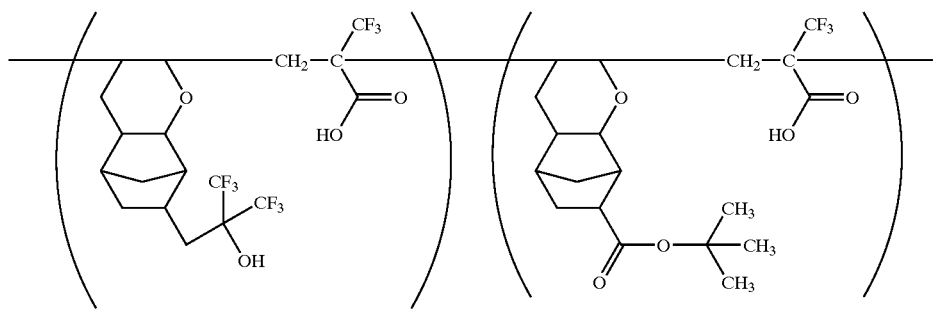

The terpolymer prepared according to Terpolymer Synthesis Example 3-7 was dissolved in a mixture of THF and methanol (1:1, 100 ml) to form a solution. An ammonia solution (28%, 5.0 g) was then added to the solution to form a reaction solution. The reaction solution was refluxed for 5 hours to form a product solution, after which the product solution was cooled to room temperature and was neutralized (pH=7) through the drop wise addition of an acid solution (HCl, 10%). The product solution was then precipitated slowly in excessive water (X10) and filtered to separate the precipitates. The first retentate was then dissolved in THF and re-precipitated in methanol solution. The precipitated solution was filtered and the second retentate was dried in a vacuum oven maintained at 50° C. for about 24 hours to obtain a modified polymer product. This synthesis exhibited a yield of about 85% and produced a hydrolyzed terpolymer having Mw=11,700 and a polydispersity (Mw/Mn) of 1.97.

Terpolymer Synthesis Example 3-9

T-butyl 3-oxa-tricyclo [$6.2.1.0^{2,7}$]undec-4-ene-10-yl carboxylate (12.5 g), prepared according to Monomer Synthesis Example 1-1,3,4-dihydro-2H-pyran (4.2 g) and 2-trifluoromethyl methyl acrylate (15.4 g) were dissolved in THF (100 g) and placed in a reactor, after which the reactor was purged with $N_2$ gas. After adding AIBN (2 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 85% and produced a terpolymer having Mw=11,000 and a polydispersity (Mw/Mn) of 2.1.

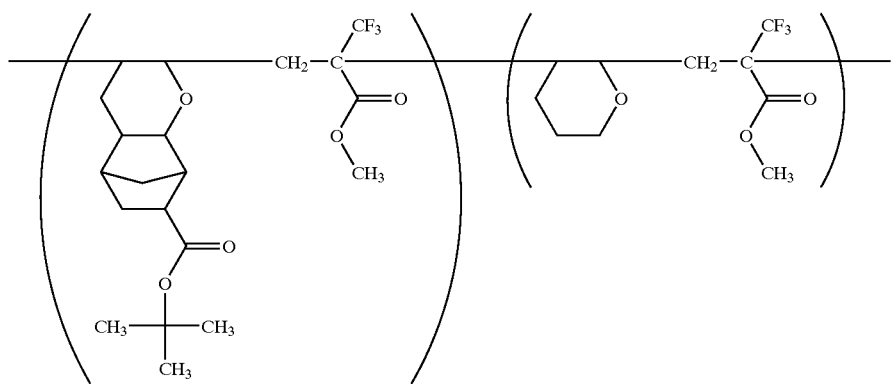

Terpolymer Synthesis Example 3-10

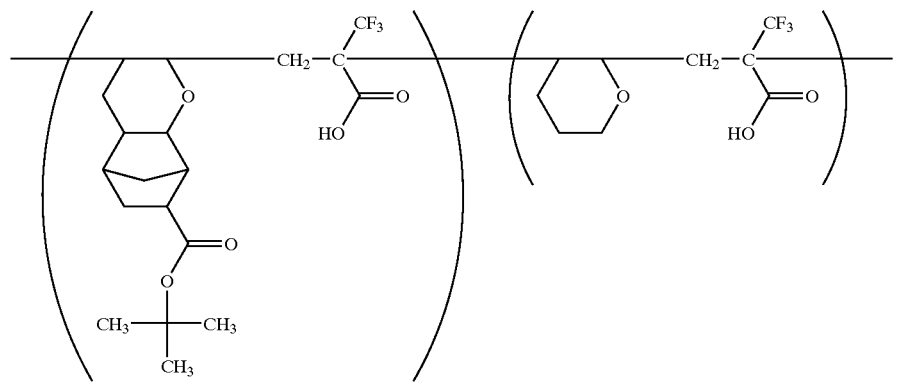

T-butyl 3-oxa-tricyclo [6.2.1.0$^{2,7}$]undec-4-ene-10-yl carboylate (12.5 g), prepared according to Monomer Synthesis Example 1-1, 3,4-dihydro-2H-pyran (4.2 g) and 2-trifluoromethyl acrylic acid (14 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 87% and produced a terpolymer having Mw=14,000 and a polydispersity (Mw/Mn) of 2.3.

Terpolymer Synthesis Example 3-11

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3, 3,4-dihydro-2H-pyran (4.2 g) and 2-trifluoromethyl t-butyl acrylate (19.6 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 95% and produced a terpolymer having Mw=19,700 and a polydispersity (Mw/Mn) of 2.2.

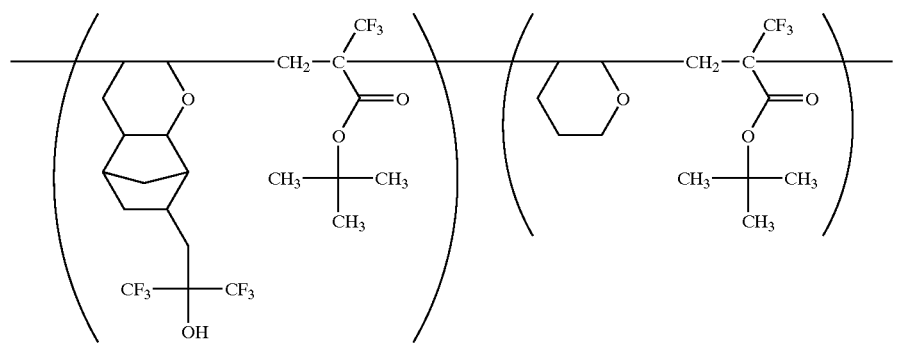

Terpolymer Synthesis Example 3-12

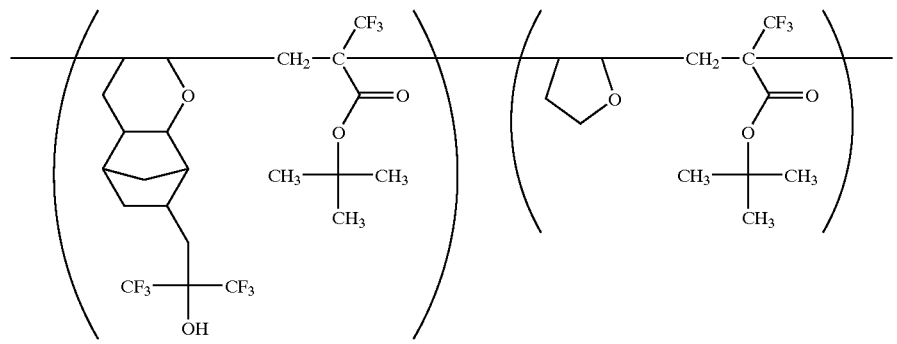

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3, 2,3-dihydrofuran (3.5 g) and 2-trifluoromethyl t-butylacrylate (19.6 g) were dissolved in THF (100 g) and placed in a reactor, after which the reactor was purged with $N_2$ gas. After adding AIBN (1 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 97% and produced a terpolymer having Mw=21,000 and a polydispersity (Mw/Mn) of 2.3.

1,1,1,3,3,3-hexafluoro-2-(3-oxa-tricyclo[6.2.1.0$^{2,7}$]undec-4-ene-10-ylmethyl)propan-2-ol (16.5 g), prepared according to Monomer Synthesis Example 1-3, 3,4-dihydro-2H-pyran (4.2 g) and α-trifluoromethyl-2-methyl-adamantane-2-yl acrylate (28.8 g) were dissolved in THF (100 g) and placed in a reactor, after which the reactor was purged with $N_2$ gas. After adding AIBN (1 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 91% and produced a terpolymer having Mw=17,100 and a polydispersity (Mw/Mn) of 2.2.

Terpolymer Synthesis Example 3-13

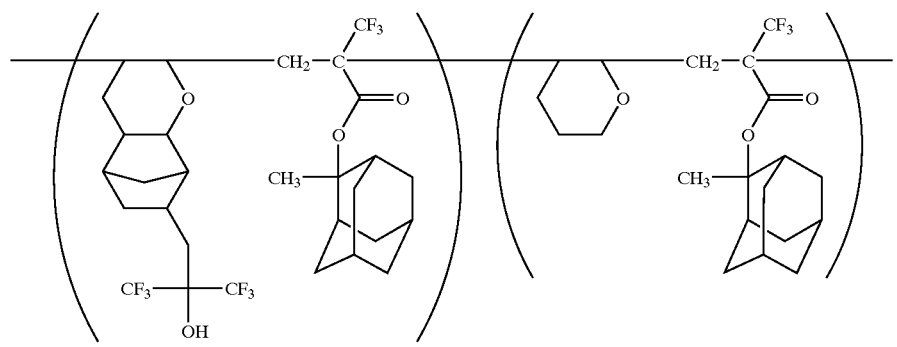

Terpolymer Synthesis Example 3-14

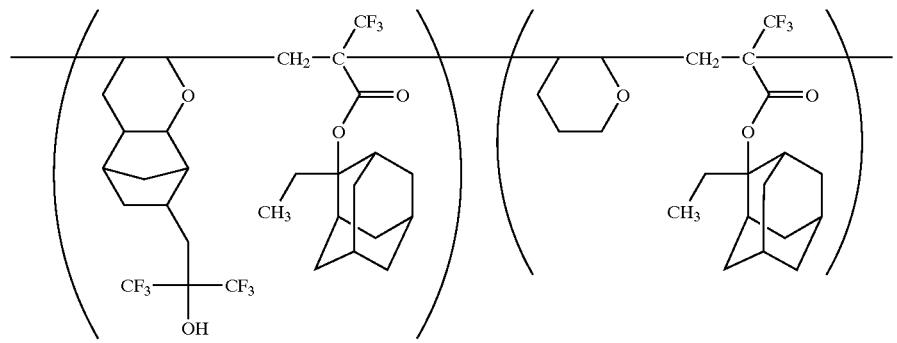

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3,3,4-dihydro-2H-pyran (4.2 g) and α-trifluoromethyl-2-ethyl-adamantane-2-yl acrylate (30.2 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 87% and produced a terpolymer having Mw=9,500 and a polydispersity (Mw/Mn) of 1.8.

Terpolymer Synthesis Example 3-15

1,1,1,3,3,3-hexafluoro-2-(3-oxa-tricyclo[6.2.1.0$^{2,7}$] undec-4-ene-10-ylmethyl)propan-2-ol (16.5 g), prepared according to Monomer Synthesis Example 1-3,3,4-dihydro-2H-pyran (4.2 g) and α-trifluoromethyl-2-propyl-adamantane-2-yl acrylate (31.6 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 85% and produced a terpolymer having Mw=10,500 and a polydispersity (Mw/Mn) of 1.7.

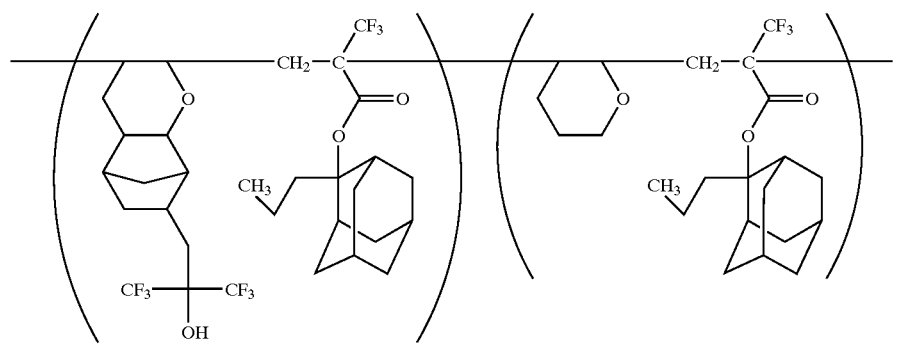

Terpolymer Synthesis Example 3-16

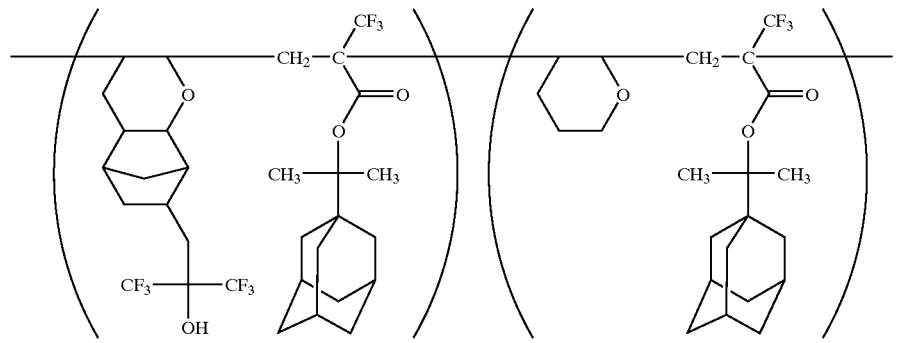

1,1,1,3,3,3-hexafluoro-2-(3-oxa-tricyclo[6.2.1.0$^{2,7}$]undec-4-ene-10-ylmethyl)propan-2-ol (16.5 g), prepared according to Monomer Synthesis Example 1-3,3,4-dihydro-2H-pyran (4.2 g) and α-trifluoromethyl-1-adamantane-1-yl-1-methyl-ethyl acrylate (31.6 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 81% and produced a terpolymer having Mw=11,500 and a polydispersity (Mw/Mn) of 1.8.

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, 3,4-dihydro-2H-pyran (4.2 g) and α-trifluoromethyl-5-oxo-4-oxa-tricyclo[4.2.1.0$^{3,7}$]non-2-yl acrylate (27.6 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 83% and produced a terpolymer having Mw=13,500 and a polydispersity (Mw/Mn) of 1.9.

Terpolymer Synthesis Example 3-17

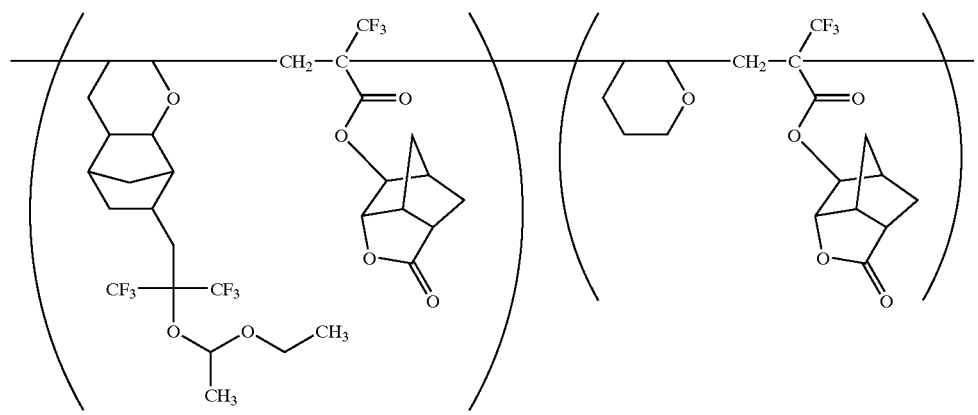

Terpolymer Synthesis Example 3-18

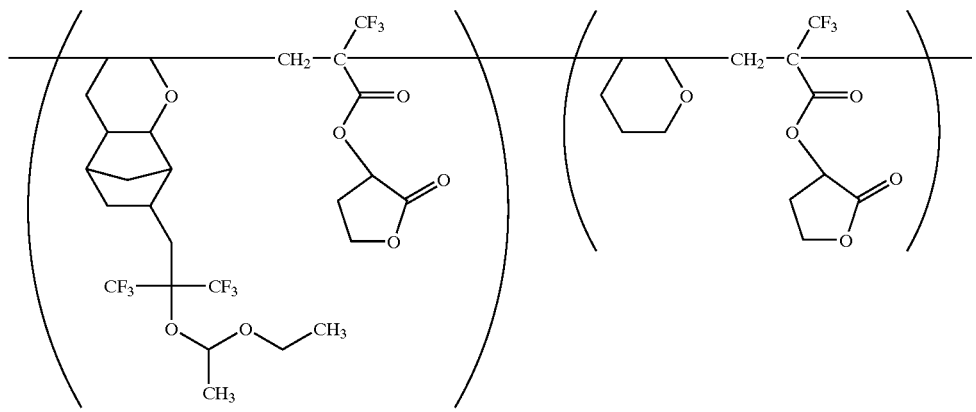

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4,3,4-dihydro-2H-pyran (4.2 g) and α-trifluoro-2-oxo-tetrahydro-furan-3-yl ester (22.4 g) were dissolved in THF (100 g) and placed in a reactor, after which the reactor was purged with $N_2$ gas. After adding AIBN (2 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 89% and produced a terpolymer having Mw=17,500 and a polydispersity (Mw/Mn) of 1.7.

Terpolymer Synthesis Example 3-19

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4,3,4-dihydro-2H-pyran (4.2 g) and α-trifluoromethyl-3,5-dehydroxy-adamantane-1-yl acrylate (30.6 g) were dissolved in THF (100 g) and placed in a reactor, after which the reactor was purged with $N_2$ gas. After adding AIBN (2 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 84% and produced a terpolymer having Mw=21,500 and a polydispersity (Mw/Mn) of 2.0.

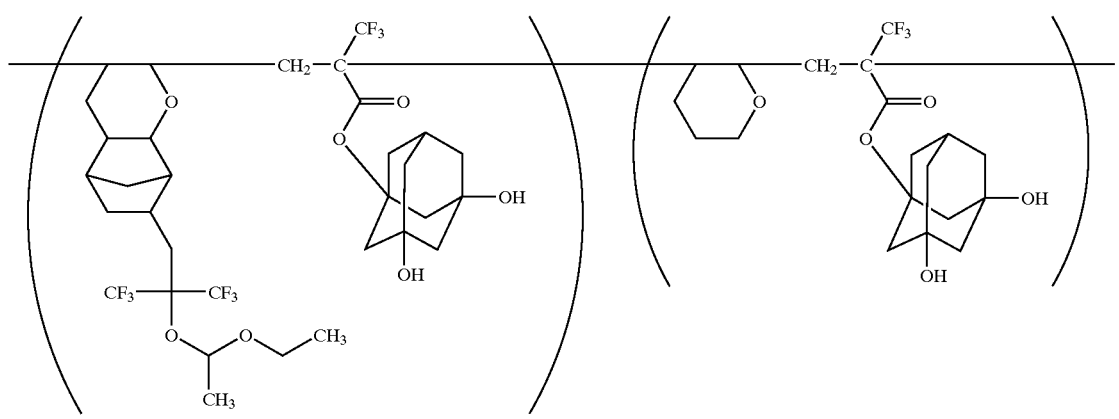

Tetrapolymer Synthesis Example 4-1

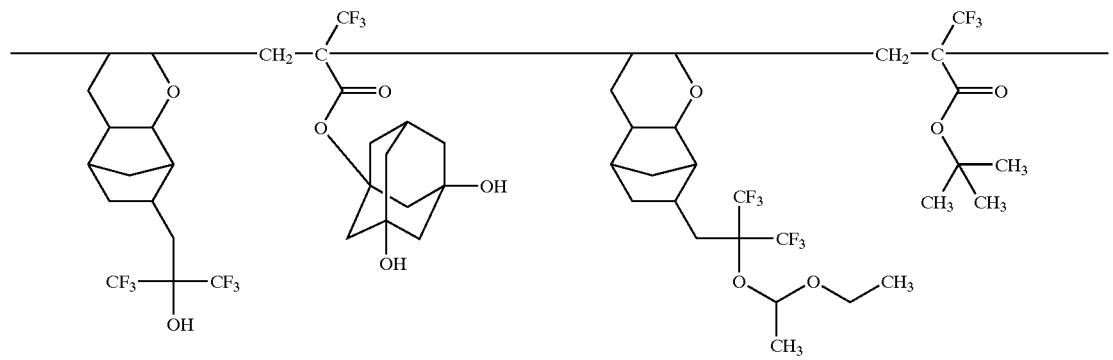

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, 1,1,1,3,3,3-hexafluoro-2-(3-oxa-tricyclo[6.2.1.0$^{2,7}$]undec-4-ene-10-ylmethyl)-propan-2-ol (16.5 g), prepared according to Monomer Synthesis Example 1-3, α-trifluoromethyl-3,5-dehydroxy-adamantane-1-yl acrylate (15.3 g) and 2-trifluoromethyl-t-butyl acrylate (9.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the tetrapolymer product. This synthesis exhibited a yield of about 78% and produced a tetrapolymer having Mw=15,500 and a polydispersity (Mw/Mn) of 2.2.

Tetrapolymer Synthesis Example 4-2

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, 1,1,1,3,3,3-hexafluoro-2-(3-oxa-tricyclo[6.2.1.0$^{2,7}$]undec-4-ene-10-ylmethyl)-propan-2-ol (16.5 g), prepared according to Monomer Synthesis Example 1-3, α-trifluoromethyl-5-oxo-4-oxa-tricyclo[4.2.1.0$^{3,7}$]non-2-yl acrylate (13.8 g) and 2-trifluoromethyl-t-butyl acrylate (9.8 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the tetrapolymer product. This synthesis exhibited a yield of about 81% and produced a tetrapolymer having Mw=19,100 and a polydispersity (Mw/Mn) of 1.9.

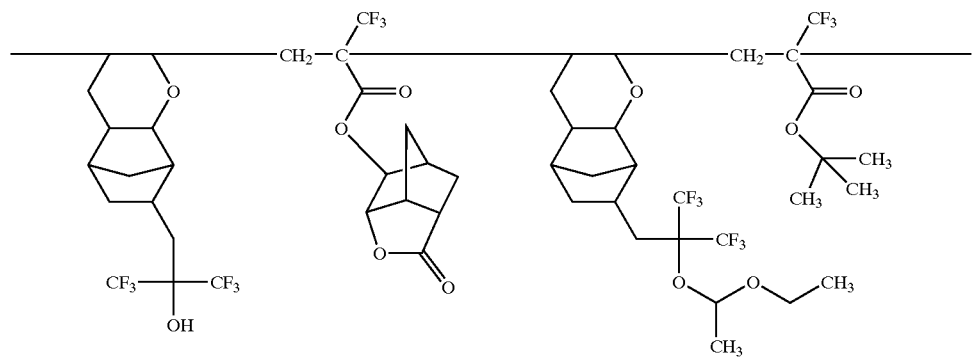

Tetrapolymer Synthesis Example 4-3

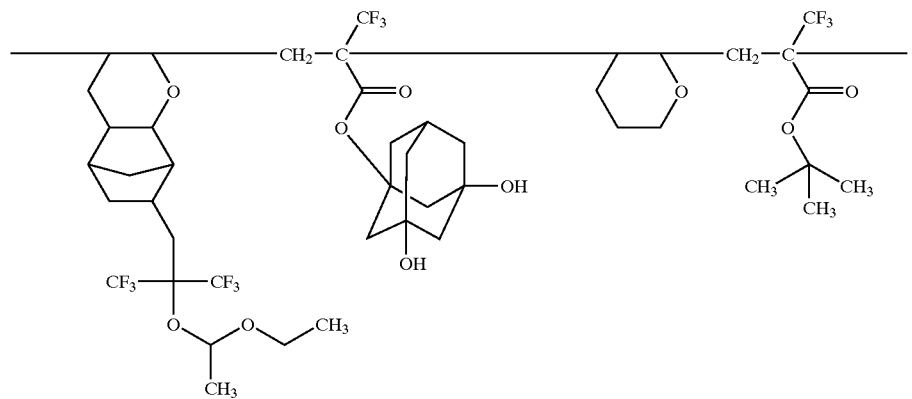

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, 3,4-dihydro-2H-pyran (4.2 g), α-trifluoromethyl-t-butyl acrylate (15.3 g) and α-trifluoromethyl-3,5-dehydroxy-adamantane-1-yl acrylate (30.6 g) were dissolved in THF (100 g) and placed in a reactor, after which the reactor was purged with $N_2$ gas. After adding AIBN (2 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 81% and produced a tetrapolymer having Mw=17,500 and a polydispersity (Mw/Mn) of 1.8.

Tetrapolymer Synthesis Example 4-4

10-[2-(1-ethoxy-ethoxy)-3,3,3-trifluoro-2-trifluoromethyl-propyl]-3-oxa-tricyclo[6.2.1.0$^{2,7}$]undec-4-ene (20.1 g), prepared according to Monomer Synthesis Example 1-4, 3,4-dihydro-2H-pyran (4.2 g), α-trifluoromethyl-5-oxo-4-oxa-tricyclo[4.2.1.0$^{3,7}$]non-2-yl acrylate (13.8 g) and 2-trifluoromethyl-t-butyl acrylate (9.8 g) were dissolved in THF (100 g) and placed in a reactor, after which the reactor was purged with $N_2$ gas. After adding AIBN (2 mol %) to the reactor, the polymerization proceeded for a polymerization time of about 12 hours at 70° C. under $N_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 81% and produced a tetrapolymer having Mw=19,100 and a polydispersity (Mw/Mn) of 1.9.

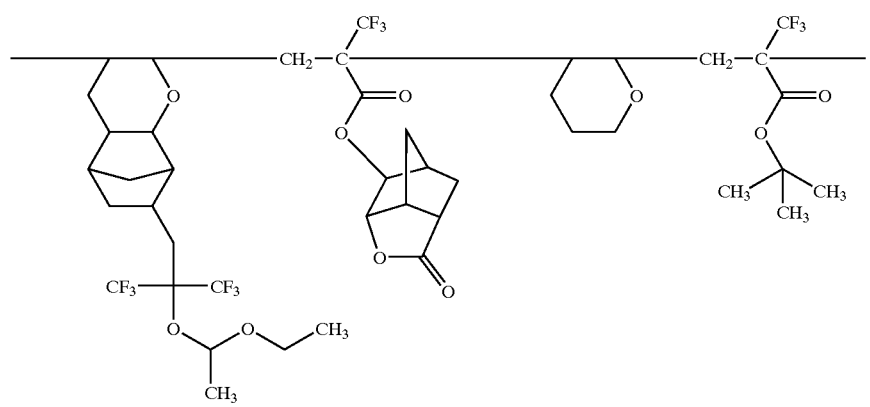

Tetrapolymer Synthesis Example 4-5

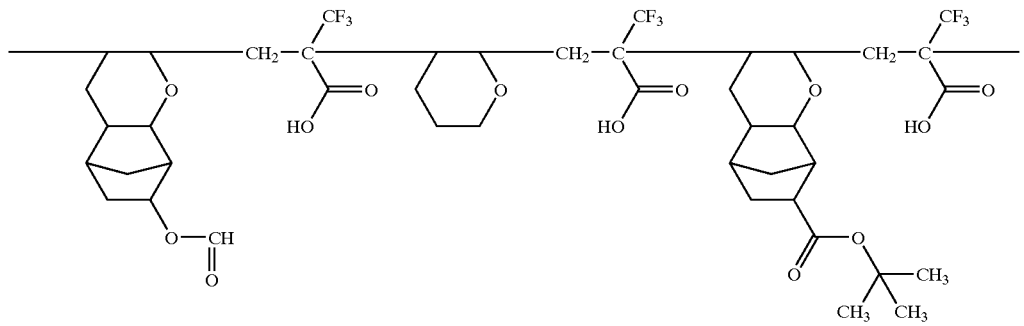

3-oxa-tricyclo [6.2.1.0$^{2,7}$]undec-4-ene-10-yl formate (9.7 g), prepared according to Monomer Synthesis Example 1-5, t-butyl oxa-tricyclo [6.2.1.0$^{2,7}$]undec-4-ene-10-yl carboxylate (12.5 g), prepared according to Monomer Synthesis Example 1-1,3,4-dihydro-2H-pyran (4.2 g), and 2-trifluoromethyl acrylic acid (21 g) were dissolved in THF (100 g) and placed in a reactor, after which the reactor was purged with N$_2$ gas. After adding AIBN (2 mol %) to the reactor, the polymerization proceeded for a polymerization time of about 12 hours at 70° C. under N$_2$ purging to obtain a product solution. After terminating the polymerization, the reaction product was precipitated slowly in excessive hexane and filtered to separate the precipitates. The first retentate was then dissolved in THF, re-precipitated in hexane and again filtered to separate the precipitates. The second retentate was then dried in a vacuum oven maintained at 50° C. for about 24 hours to obtain the terpolymer product. This synthesis exhibited a yield of about 66% and produced a tetrapolymer having Mw=13,700 and a polydispersity (Mw/Mn) of 2.1.

Tetrapolymer Synthesis Example 4-6

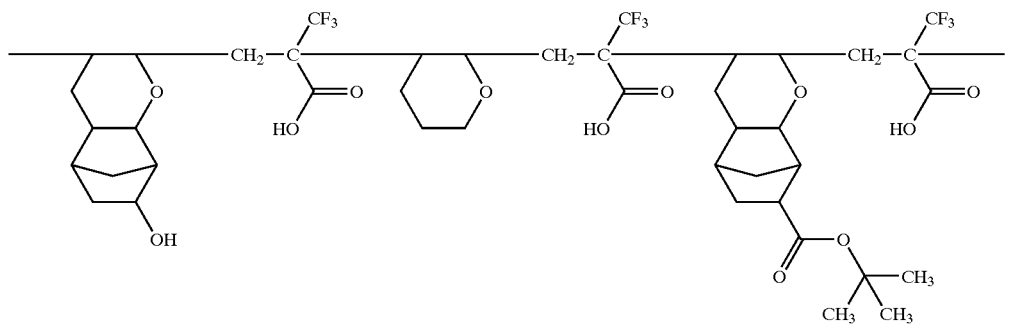

The tetrapolymer prepared according to Tetrapolymer Synthesis Example 4-5 was dissolved in a mixture of THF and methanol (1:1, 100 ml) to form a solution. An ammonia solution (28%, 5.0 g) was then added to the solution to form a reaction solution. The reaction solution was refluxed for 5 hours to form a product solution, after which the product solution was cooled to room temperature and was neutralized (pH=7) through the drop wise addition of an acid solution (HCl, 10%). The product solution was then precipitated slowly in excessive water (X10) and filtered to separate the precipitates. The first retentate was then dissolved in THF and re-precipitated in methanol solution. The precipitated solution was filtered and the second retentate was dried in a vacuum oven maintained at 50° C. for about 24 hours to obtain a modified polymer product. This synthesis exhibited a yield of about 85% and produced a hydrolyzed tetrapolymer having Mw=13,500 and a polydispersity (Mw/Mn) of 1.95.

As noted above, polymers prepared according to the invention may be utilized for producing the photoresist compositions of the present invention. Provided below are a series of examples illustrating the preparation of certain exemplary photoresist compositions according to the present invention. Those of ordinary skill in the art will appreciate that these examples are illustrative only and do not attempt to illustrate each of the acceptable photoresist compositions.

Those of ordinary skill in the art will appreciate that the formulas provided above, particularly with respect to the various terpolymers and tetrapolymers, although generally illustrating the various monomer components, should not be interpreted as accurately representing polymer structure. Indeed, depending on the specific mixture of starting compounds and synthesis conditions, the molar fraction and actual sequence of the various monomers in the resulting polymer may vary widely. In general, however, each of the multi-ring alkenyl ether(s) and/or dihydropyran(s) monomers will be separated by an α-fluorinated acrylate monomer as a function of the radical (cationic) polymerization.

Preparation and Verification of Exemplary Resist Compositions

Exemplary Photoresist Composition R-1

An exemplary photoresist composition may be prepared by dissolving one or more of the copolymers (1 g) described above in connection with the Copolymer Synthesis Examples 2-1 to 2-3, triphenylsulfonium nonaflate (0.03 g) as a PAG, and triethanolamine (2 mg) as an organic base in cyclohexanone (8.0 g) to form a solution. This solution was then filtered using a membrane filter of 0.2 μm to obtain an exemplary photoresist composition, R-1.

The R-1 photoresist composition was then applied onto a bare Si-wafer coated with organic ARC to form a 0.27 μm-thick photoresist film, after which the photoresist film was pre-baked at a temperature of 120° C. for 90 seconds, and exposed using an ArF excimer laser exposure apparatus (0.78 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.11 μm could be formed using an exposure intensity of 10 to 30 mJ/cm$^2$.

Exemplary Photoresist Composition R-2

An exemplary photoresist composition may be prepared by dissolving one or more of the copolymers (1 g) described above in connection with the Copolymer Synthesis Examples 2-4 to 2-14, triphenylsulfonium nonaflate (0.03 g) as a PAG, and triethanolamine (2 mg) as an organic base in cyclohexanone (8.0 g) to form a solution. This solution was then filtered using a membrane filter of 0.2 μm to obtain an exemplary photoresist composition, R-2.

The R-2 photoresist composition was then applied onto a bare Si-wafer coated with organic ARC to form a 0.27 μm-thick photoresist film, after which the photoresist film was pre-baked at a temperature of 120° C. for 90 seconds, and exposed using an ArF excimer laser exposure apparatus (0.80 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.18 μm could be formed using an exposure intensity of 10 to 30 mJ/cm$^2$.

Exemplary Photoresist Composition R-3

An exemplary photoresist composition may be prepared by dissolving one or more of the copolymers (1 g) described above in connection with the Copolymer Synthesis Examples 24 to 2-14, triphenylsulfonium nonaflate (0.03 g) as a PAG, and triethanolamine (2 mg) as an organic base in cyclohexanone (8.0 g) to form a solution. This solution was then filtered using a membrane filter of 0.2 μm to obtain an exemplary photoresist composition, R-3.

The R-3 photoresist composition was then applied onto a bare Si-wafer coated with organic ARC to form a 0.23 μm-thick photoresist film, after which the photoresist film was pre-baked at a temperature of 120° C. for 90 seconds, and exposed using an ArF excimer laser exposure apparatus (0.85 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.18 μm could be formed using an exposure intensity of 10 to 30 mJ/cm$^2$.

Exemplary Photoresist Composition R-4

An exemplary photoresist composition may be prepared by dissolving one or more of the terpolymers (1 g) described above in connection with the Terpolymer Synthesis Examples 3-1 to 3-4, triphenylsulfonium triflate (0.02 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-4.

The R-4 photoresist composition was then applied onto a bare Si-wafer coated with organic ARC to form a 0.3 μm-thick photoresist film, after which the photoresist film was pre-baked at a temperature of 120° C. for 90 seconds, and exposed using an ArF excimer laser exposure apparatus (0.6 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.15 μm could be formed using an exposure intensity of 10 to 30 mJ/cm$^2$.

Exemplary Photoresist Composition R-5

An exemplary photoresist composition may be prepared by dissolving one or more of the terpolymers (1 g) described above in connection with the Terpolymer Synthesis Examples 3-5 to 3-8, triphenylsulfonium perfluorobutan sulfonate (0.03 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-5.

The R-5 photoresist composition was then applied onto a bare Si-wafer coated with organic ARC to form a 0.3 μm-thick photoresist film, after which the photoresist film was pre-baked at a temperature of 120° C. for 90 seconds, and exposed using an ArF excimer laser exposure apparatus (0.6 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.15 μm could be formed using an exposure intensity of 10 to 30 mJ/cm$^2$.

Exemplary Photoresist Composition R-6

An exemplary photoresist composition may be prepared by dissolving one or more of the terpolymers (1 g) described above in connection with the Terpolymer Synthesis Examples 3-9 or 3-10, triphenylsulfonium nonaflate (0.15 g) and triphenylsulfonium triflate (0.1 g) as PAGs and triisodecyl amine (2 mg) as an organic base in cyclohexanone (8.0 g) to form a solution. This solution was then filtered using a membrane filter of 0.2 μm to obtain an exemplary photoresist composition, R-6.

The R-6 photoresist composition was then applied onto a bare Si-wafer coated with organic ARC to form a 0.2 μm-thick photoresist film, after which the photoresist film was pre-baked at a temperature of 120° C. for 90 seconds, and exposed using an ArF excimer laser exposure apparatus (0.85 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.15 μm could be formed using an exposure intensity of 10 to 30 mJ/cm$^2$.

Exemplary Photoresist Composition R-7

An exemplary photoresist composition may be prepared by dissolving one or more of the terpolymers (1 g) described above in connection with the Terpolymer Synthesis Examples 3-9 or 3-10, triphenylsulfonium nonaflate (0.03 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-7.

The R-7 photoresist composition was then applied onto a bare Si-wafer coated with organic ARC to form a 0.3

μm-thick photoresist film, after which the photoresist film was pre-baked at a temperature of 120° C. for 90 seconds, and exposed using an ArF excimer laser exposure apparatus (0.75 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.12 μm could be formed using an exposure intensity of 10 to 30 mJ/cm$^2$.

Exemplary Photoresist Composition R-8

An exemplary photoresist composition may be prepared by dissolving one or more of the terpolymers (1 g) described above in connection with the Terpolymer Synthesis Examples 3-9 or 3-10, triphenylsulfonium nonaflate (0.03 g) as a PAG and triisodecyl amine (2 mg) as an organic base in propylene glycol monomethyl ether acetate (8.0 g) to form a solution. This solution was then filtered using a membrane filter of 0.2 μm to obtain an exemplary photoresist composition, R-8.

The R-8 photoresist composition was then applied onto a bare Si-wafer coated with organic ARC to form a 0.25 μm-thick photoresist film, after which the photoresist film was pre-baked at a temperature of 120° C. for 90 seconds, and exposed using an ArF excimer laser exposure apparatus (0.80 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.18 μm could be formed using an exposure intensity of 10 to 30 mJ/cm$^2$.

Exemplary Photoresist Composition R-9

An exemplary photoresist composition may be prepared by dissolving one or more of the tetrapolymers (1 g) described above in connection with the Tetrapolymer Synthesis Examples 4-1 to 4-6, triphenylsulfonium nonaflate (0.03 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-9.

The R-9 photoresist composition was then applied onto a bare Si-wafer coated with organic ARC to form a 0.25 μm-thick photoresist film, after which the photoresist film was pre-baked at a temperature of 120° C. for 90 seconds, and exposed using an ArF excimer laser exposure apparatus (0.60 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.15 μm could be formed using an exposure intensity of 10 to 30 mJ/cm$^2$.

Exemplary Photoresist Composition R-10

An exemplary photoresist composition may be prepared by dissolving one or more of the tetrapolymers (1 g) described above in connection with the Tetrapolymer Synthesis Examples 4-1 to 4-6, triphenylsulfonium nonaflate (0.03 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-10.

The R-10 photoresist composition was then applied onto a bare Si-wafer coated with organic ARC to form a 0.3 μm-thick photoresist film, after which the photoresist film was pre-baked at a temperature of 120° C. for 90 seconds, and exposed using an ArF excimer laser exposure apparatus (0.80 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.18 μm could be formed using an exposure intensity of 10 to 30 mJ/cm$^2$.

Exemplary Photoresist Composition R-11

An exemplary photoresist composition may be prepared by dissolving one or more of the tetrapolymers (1 g) described above in connection with the Tetrapolymer Synthesis Examples 4-1 to 4-6, triphenylsulfonium nonaflate (0.03 g) as a PAG and triisodecyl amine (2 mg) as an organic base in cyclohexanone (8.0 g) to form a solution. This solution was then filtered using a membrane filter of 0.2 μm to obtain an exemplary photoresist composition, R-11.

The R-11 photoresist composition was then applied onto a bare Si-wafer coated with organic ARC to form a 0.2 μm-thick photoresist film, after which the photoresist film was pre-baked at a temperature of 120° C. for 90 seconds, and exposed using an ArF excimer laser exposure apparatus (0.85 NA). After completing the exposure, the exposed photoresist film was subjected to a post-exposure bake (PEB) at 120° C. for 90 seconds and developed for 60 seconds using a 2.38 wt % aqueous solution of tetramethyl ammonium hydroxide to form a photoresist pattern. Inspection of the developed photoresist pattern confirmed that a clear line/space (L/S) pattern of 0.15 μm could be formed using an exposure intensity of 10 to 30 mJ/cm$^2$ The exemplary photosensitive polymers according to the present invention will include at least two monomers that include a multi-ring alkenyl ether and an α-fluorinated acrylate that will tend to exhibit improved transmittance and improved resistance to dry etching processes. The exemplary photosensitive polymers according to the present invention will also typically include at least one additional monomer, such as a pyran ring structure in its backbone, for the purpose of improving adhesion to underlying layers. Further, because the exemplary polymers can be synthesized in a relatively straightforward manner, a range of monomers having various structures can be prepared using a variety of available norbornene derivatives to adapt the characteristics of the photosensitive polymers as needed. Further, because the exemplary polymers can be synthesized without the use of any heavy metal catalyst using radical (cationic) polymerization, photoresist compositions incorporating the exemplary photosensitive polymers may be used in semiconductor manufacturing processes to reduce the risk of heavy-metal contamination when compared with polymers prepared using conventional polymerization of norbornene derivatives while still providing desirable resistance to dry etching and adhesive characteristics.

Also, exemplary photosensitive compositions incorporating the exemplary photosensitive polymer(s) according to the present invention can be utilized with various light sources including KrF excimer lasers (248 nm), ArF excimer lasers (193 nm) and F$_2$ excimer lasers (157 nm). In particular, in the case of using the F$_2$ excimer lasers having a wavelength of 157 nm, resist compositions according to the present invention can reduce or eliminate the need to incorporate functional group(s) that would tend to reduce transmittance, such as phenyl and carboxyl groups, and can, instead, incorporate fluorinated hydrocarbon groups that provide improved transmittance at 157 nm by a simple substitution method. The exemplary photosensitive polymers, therefore, may be adapted to improve transmittance and increase the resolution of photoresist compositions.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A photosensitive copolymer including an α-fluorinated acrylate monomer and an alkenyl ether monomer having the formula I

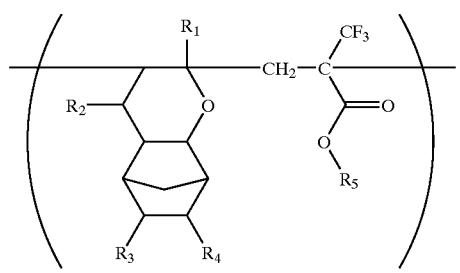

wherein
$R_1$ and $R_2$ are independently selected from a group consisting of hydrogen and methyl;
$R_3$ and $R_4$ are independently selected from a group consisting of hydrogen, hydroxy, alkyl, cycloalkyl, haloalkyl, alkoxy, carboxyl, carbonyl, ester and acid labile groups; and
$R_5$ is selected from a group consisting of hydrogen, hydroxy, substituted and unsubstituted alkyls, substituted and unsubstituted cycloalkyls, substituted and unsubstituted alkoxys, substituted and unsubstituted heterocyclics, and acid labile groups;
further wherein
at least one of $R_3$, $R_4$ and $R_5$ include an acid labile group.

2. A photosensitive copolymer according to claim 1, wherein:
the acid labile group is a hydrocarbon or a substituted hydrocarbon having at least 4 and no more than 20 carbon atoms.

3. A photosensitive copolymer according to claim 1, wherein:
the copolymer includes an acid labile group selected from a group consisting of t-butyl, tetrahydropyranyl, and substituted or unsubstituted alicyclic hydrocarbons having 6-12 carbon atoms.

4. A photosensitive copolymer according to claim 1, wherein:
the copolymer includes an acid labile group selected from a group consisting of 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

5. A photosensitive copolymer according to claim 1, wherein:
the copolymer includes an alkenyl ether monomer selected from the group consisting of alkenyl ether monomers represented by the formulas:

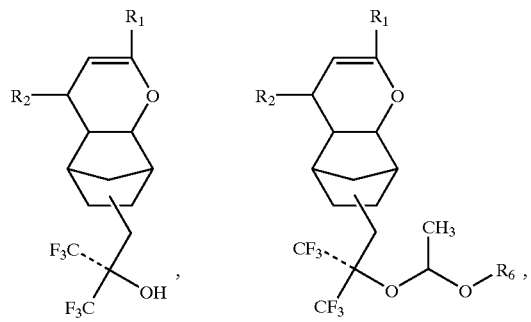

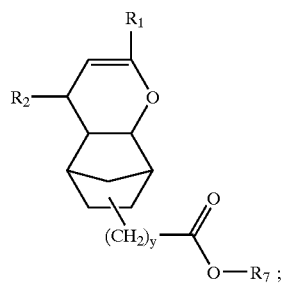

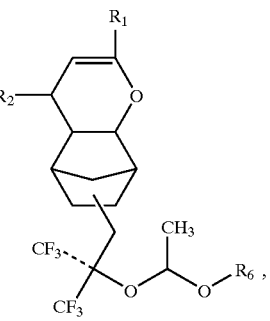

wherein
y is 0, 1 or 2;
$R_6$ is selected from a group consisting of alkyls and substituted alkyls having at least one and no more than 20 carbon atoms; and
$R_7$ is an acid labile group including a hydrocarbon or a substituted hydrocarbon having at least 4 and no more than 20 carbons.

6. A photosensitive copolymer according to claim 5, wherein:
$R_7$ is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

7. A photosensitive copolymer according to claim 1, wherein:
at least one half of the haloalkyls included in the copolymer are fluoroalkyls.

8. A photosensitive copolymer according to claim 1, wherein:

the copolymer has a Mw of between about 7,000 and 25,000; and a polydispersity of between about 1.7 and about 2.5.

9. A photosensitive copolymer according to claim 1, wherein:

the copolymer has a Mw of between about 12,000 and 19,000; and a polydispersity of between about 1.7 and about 2.5.

10. A photosensitive copolymer according to claim 1, wherein:

the copolymer includes a substituted or unsubstituted α-fluorinated acrylate monomer selected from the group represented by the formulas:

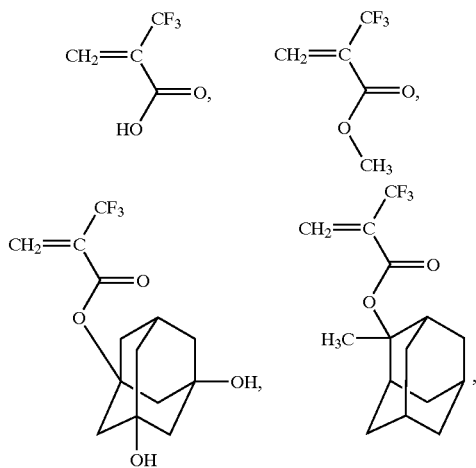

-continued

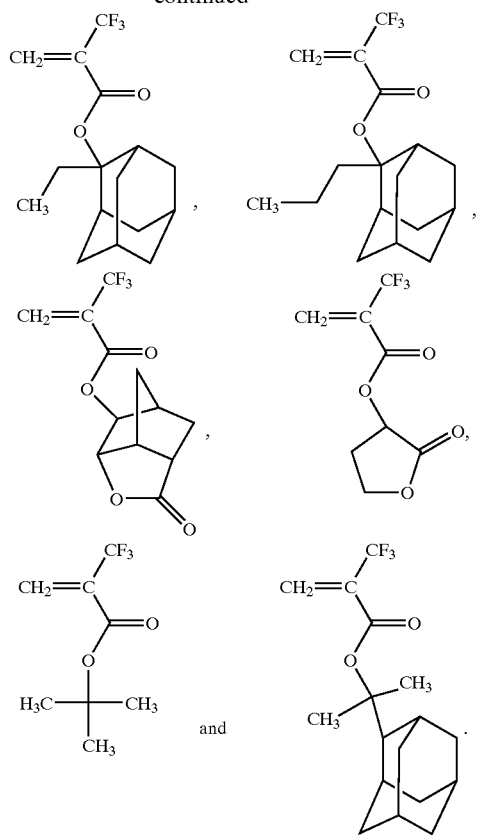

11. A photosensitive copolymer according to claim 1, wherein:
at least one half of the haloalkyls included in the terpolymer are fluoroalkyls.

12. A photosensitive terpolymer including an α-fluorinated acrylate monomer, a first alkenyl ether monomer and a second alkenyl ether monomer having the formula II

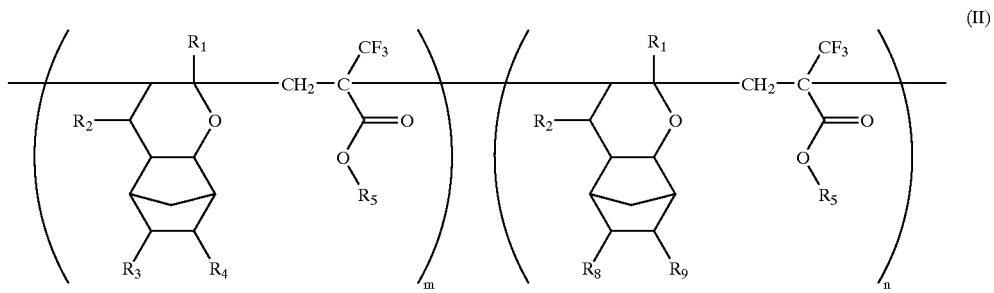

(II)

wherein
m+n equals 1;
$0.01 \leq m/(m+n) \leq 0.8$;
$R_1$ and $R_2$ are independently selected from a group consisting of hydrogen and methyl;
$R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups; and
$R_5$ is selected from a group consisting of hydrogen, hydroxy, alkyl, cycloalkyl, haloalkyl, alkoxy, carboxyl, carbonyl, ester and acid labile groups; and further wherein
the terpolymer includes at least one acid labile group and the first alkenyl ether monomer and the second alkenyl ether monomer are different.

13. A photosensitive terpolymer including an α-fluorinated acrylate monomer, a first alkenyl ether monomer and a second alkenyl ether monomer according to claim 12, wherein:
m/(m+n) is between about 0.3 and 0.5.

14. A photosensitive terpolymer according to claim 12, wherein:
the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

15. A photosensitive terpolymer according to claim 12, wherein:
the terpolymer has a Mw of between about 8,000 and 25,000; and
a polydispersity of between about 1.6 and about 2.5.

16. A photosensitive terpolymer according to claim 12, wherein:
the terpolymer has a Mw of between about 10,000 and 15,000; and
a polydispersity of between about 1.8 and about 2.3.

17. A photosensitive terpolymer including an α-fluorinated acrylate monomer, an alkenyl ether monomer and a dihydropyran having the formula III haloalkyl, alkoxy, carboxyl, carbonyl, ester and acid labile groups; and
$R_5$ is selected from a group consisting of hydrogen, hydroxy, alkyl, cycloalkyl, haloalkyl, alkoxy, carboxyl, carbonyl, ester and acid labile groups; and
further wherein
at least one of $R_3$, $R_4$ and $R_5$ includes an acid labile group.

18. A photosensitive terpolymer according to claim 17, wherein:
m/(m+n) is between about 0.3 and 0.5.

19. A photosensitive terpolymer according to claim 17, wherein:
the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

20. A photosensitive terpolymer according to claim 17, wherein:
at least one half of the haloalkyls included in the terpolymer are fluoroalkyls.

21. A photosensitive terpolymer according to claim 17, wherein:
the terpolymer has a Mw of between about 8,000 and 25,000; and
a polydispersity of between about 1.6 and about 2.5.

22. A photosensitive terpolymer according to claim 17, wherein:
the terpolymer has a Mw of between about 10,000 and 15,000; and

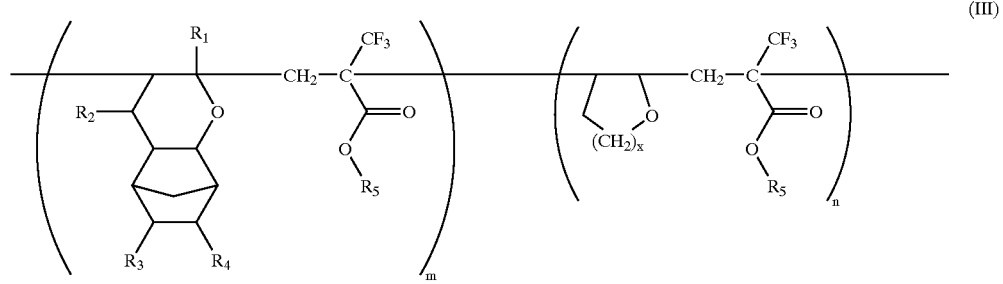

wherein
x is 1 or 2;
m+n equals 1;
0.01 ≤ m/(m+n) ≤ 0.8; and wherein
$R_1$ and $R_2$ are independently selected from a group consisting of hydrogen and methyl;
$R_3$ and $R_4$ are independently selected from a group consisting of hydrogen, hydroxy, alkyl, cycloalkyl, a polydispersity of between about 1.8 and about 2.3.

23. A photosensitive terpolymer according to claim 17, wherein:
$R_5$ is selected from a group consisting of t-butyl, substituted cyclohexyl, 2-methyl-2-norbornyl, 2-methyl-2-isobornyl, 2-ethyl-2-isobornyl, 8-methyl-8-tricyclo[5.2.1.0$^{2,6}$]decanyl, 2-methyl-2-adamantyl and 2-ethyl-2-adamantyl.

24. A photosensitive terpolymer including first and second α-fluorinated acrylate monomers and an alkenyl ether monomer having the formula IIB

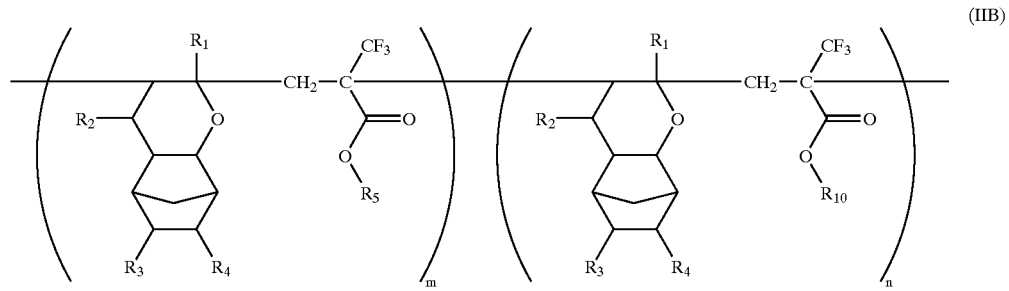

(IIB)

wherein
m+n equals 1;
$0.01 \leq m/(m+n) \leq 0.8$
$R_1$ and $R_2$ are independently selected from a group consisting of hydrogen and methyl;
$R_3$ and $R_4$ are independently selected from a group consisting of hydrogen, hydroxy, alkyl, cycloalkyl, haloalkyl, alkoxy, carboxyl, carbonyl, ester and acid labile groups; and
$R_5$ and $R_{10}$ are independently is selected from a group consisting of hydrogen, hydroxy, alkyl, cycloalkyl, haloalkyl, alkoxy, carboxyl, carbonyl, ester and acid labile groups;
further wherein
the terpolymer includes at least one acid labile group and the first α-fluorinated acrylate monomer and the second α-fluorinated acrylate monomer are different.

25. A photosensitive terpolymer according to claim 24, wherein:
m/(m+n) is between about 0.3 and 0.5.

26. A photosensitive terpolymer according to claim 24, wherein:
the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$] decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

27. A photosensitive terpolymer according to claim 24, wherein:
at least one half of the haloalkyls included in the copolymer are fluoroalkyls.

28. A photosensitive terpolymer according to claim 24, wherein:
the terpolymer has a Mw of between about 8,000 and 25,000; and
a polydispersity of between about 1.6 and about 2.5.

29. A photosensitive copolymer according to claim 24, wherein:
the copolymer has a Mw of between about 10,000 and 15,000; and
a polydispersity of between about 1.8 and about 2.3.

30. A photosensitive tetrapolymer including first and second α-fluorinated acrylate monomers and first and second alkenyl ether monomers having the formula IV

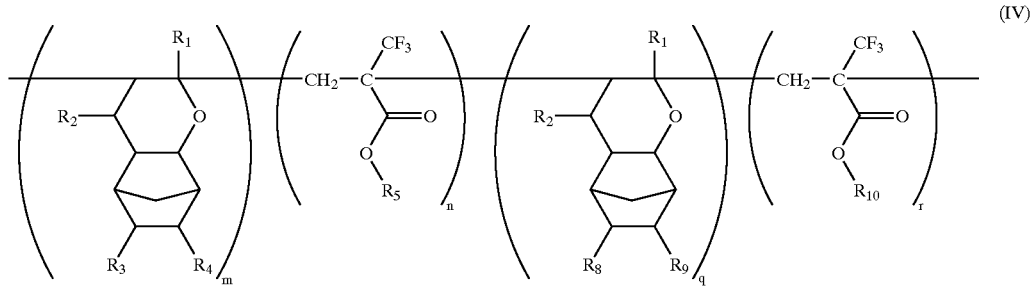

(IV)

wherein
m+n+q+r=1;
m+q=n+r;
$0.01 \leq m/(m+q) \leq 0.8$;
$0.01 \leq n/(n+r) \leq 0.8$;
$R_1$ and $R_2$ are independently selected from a group consisting of hydrogen and methyl;
$R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups; and
$R_5$ and $R_{10}$ are independently selected from a group consisting of hydrogen, hydroxy, alkyl, cycloalkyl, haloalkyl, alkoxy, carboxyl, carbonyl, ester and acid labile groups; and further wherein the tetrapolymer includes at least one monomer that includes an acid labile group, the first alkenynl ether monomer and the second alkenynl ether monomer are different, and the first and second α-fluorinated acrylate monomers are different.

31. A photosensitive tetrapolymer according to claim 30, wherein:

$m/(m+q)$ is between about 0.3 and 0.5.

32. A photosensitive tetrapolymer according to claim 30, wherein:

the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$] decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

33. A photosensitive tetrapolymer according to claim 30, wherein:

the tetrapolymer has a Mw of between about 10,000 and 20,000; and a polydispersity of between about 1.7 and about 2.5.

34. A photosensitive tetrapolymer according to claim 30, wherein:

the copolymer has a Mw of between about 13,000 and 19,000; and a polydispersity of between about 1.8 and about 2.2.

35. A photosensitive pentapolymer including first and second α-fluorinated acrylate monomers, first and second alkenyl ether monomers and a dihydrofuran having the formula V:

$R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups; and $R_5$ and $R_{10}$ are independently selected from a group consisting of hydrogen, hydroxy, alkyl, cycloalkyl, haloalkyl, alkoxy, carboxyl, carbonyl, ester and acid labile groups; and further wherein the tetrapolymer includes at least one monomer that includes an acid labile group, the first alkenyl ether monomer and the second alkenyl ether monomer are different, and the first and second α-fluorinated acrylate monomers are different.

36. A photosensitive pentapolymer according to claim 35, wherein:

$m/(m+q+s)$ is between about 0.3 and 0.5; and $q/(m+q+s)$ is between about 0.3 and 0.5.

37. A photosensitive pentapolymer according to claim 35, wherein:

$m/(m+q+s)$ is between about 0.3 and 0.5; and $s/(m+q+s)$ is between about 0.3 and 0.5.

38. A photosensitive pentapolymer according to claim 35, wherein:

the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$] decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

39. A photosensitive pentapolymer according to claim 35, wherein:

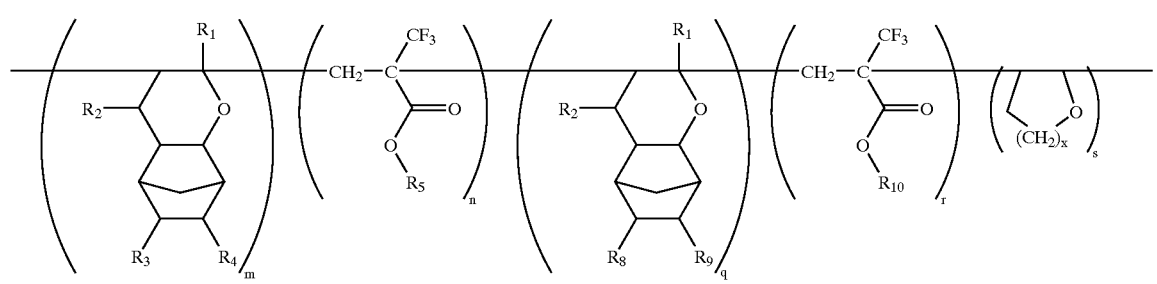

(V)

wherein x is 1 or 2;

$m+n+q+r+s=1$;

$m+q+s=n+r$;

$0.01 \leq m/(m+q+s) \leq 0.8$;

$0.01 \leq n/(n+r) \leq 0.8$;

$0.01 \leq q/(m+q+s) \leq 0.8$; and $R_1$ and $R_2$ are independently selected from a group consisting of hydrogen and methyl;

the pentapolymer has a Mw of between about 7,000 and 25,000; and a polydispersity of between about 1.7 and about 2.5.

40. A photosensitive pentapolymer according to claim 35, wherein:

the copolymer has a Mw of between about 12,000 and 19,000; and a polydispersity of between about 1.8 and about 2.3.

41. A photosensitive polymer including at least one α-fluorinated acrylate monomer and at least one alkenyl ether monomer having the formula V:

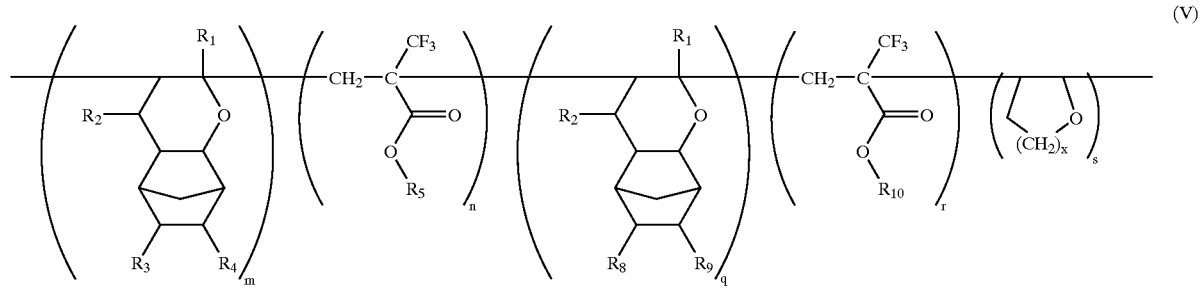

(V)

wherein
x is 1 or 2;
m+n+q+r+s=1;
m+q+s=n+r;
$0.01 \leq m/(m+q+s) \leq 0.8$;
$0.01 \leq n/(n+r) \leq 0.8$;
$0 \leq q/(m+q+s) \leq 0.8$; and
$0 \leq r/(n+r) \leq 0.8$;
$0 \leq s/(m+q+s) \leq 0.8$; and $R_1$ and $R_2$ are independently selected from a group consisting of hydrogen and methyl;

$R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups; and $R_5$ and $R_{10}$ are different and are independently selected from a group consisting of hydrogen, hydroxy, alkyl, cycloalkyl, haloalkyl, alkoxy, carboxyl, carbonyl, ester and acid labile groups; and further wherein the photosensitive polymer includes at least one monomer that includes an acid labile group.

42. A photosensitive polymer according to claim 41, wherein:

each acid labile group is selected from a group consisting of substituted and unsubstituted t-butyl, substituted and unsubstituted cyclohexyl, substituted and unsubstituted heterocyclo, substituted and unsubstituted 1-methyl-1-cyclohexyl, substituted and unsubstituted 1-ethyl-1-cyclohexyl, substituted and unsubstituted 2-methyl-2-norbornyl, substituted and unsubstituted 2-ethyl-2-norbornyl, substituted and unsubstituted 2-methyl-2-isobornyl, substituted and unsubstituted 2-ethyl-2-isobornyl, substituted and unsubstituted 8-methyl-8-tricyclo[$5.2.1.0^{2,6}$]decanyl, substituted and unsubstituted 8-ethyl-8-tricyclo[$5.2.1.0^{2,6}$]decanyl, substituted and unsubstituted 2-methyl-2-adamantyl, substituted and unsubstituted 2-ethyl-2-adamantyl, substituted and unsubstituted 1-adamantyl-1-methylethyl, substituted and unsubstituted 2-methyl-2-fenchyl and substituted and unsubstituted 2-ethyl-2-fenchyl groups.

43. A photosensitive polymer according to claim 41, wherein:

the photosensitive polymer includes a mixture of at least two different photosensitive polymers, each of which has a Mw of between about 3,000 and 100,000; and a polydispersity of between about 1.5 and about 3.0.

44. A photoresist composition according to claim 41, wherein:

the photosensitive polymer has a Mw of between about 7,000 and 25,000; and
a polydispersity of between about 1.7 and about 2.3.

45. A method of forming a photosensitive polymer comprising:

combining at least one alkenyl ether monomer selected from the group consisting of alkenyl ether monomers represented by the formulas:

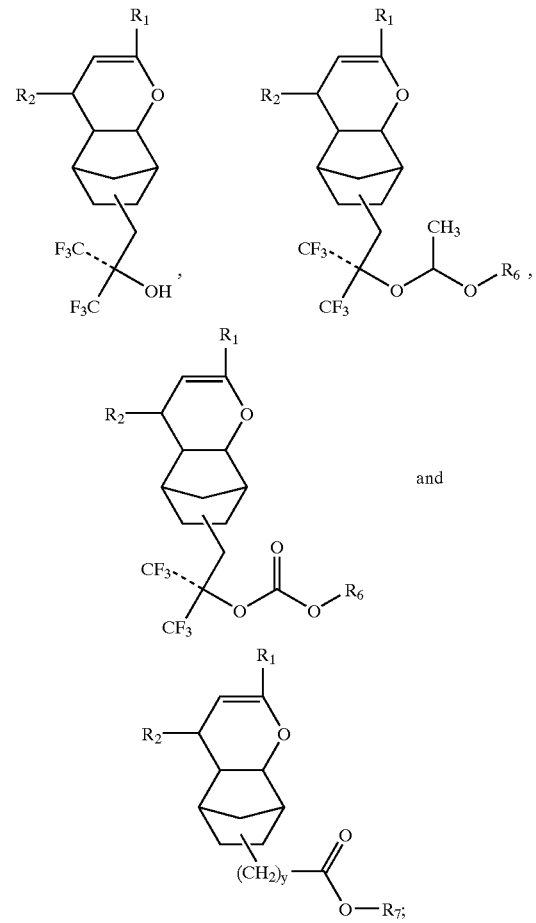

and wherein
y is 0, 1 or 2;
$R_6$ is selected from a group consisting of alkyls and substituted alkyls having at least one and no more than 20 carbon atoms; and R₇ is an acid labile group including a hydrocarbon or a substituted hydrocarbon having at least 4 and no more then 20 carbons; and a substituted or unsubstituted α-fluorinated acrylate monomer selected from the group represented by the formulas:

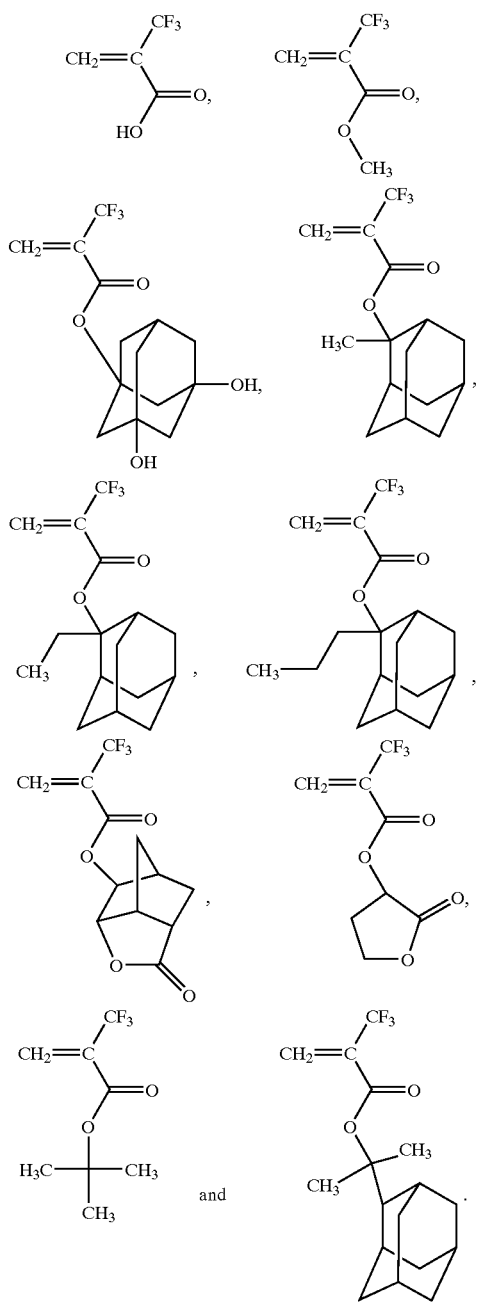

in a solvent to form a polymerization solution, the polymerization solution being substantially free of heavy metals;

heating the polymerization solution to a polymerization temperature for a polymerization period sufficient to cause the radical polymerization of the α-fluorinated acrylate and alkenyl ether monomers.

46. A method of forming a photosensitive polymer according to claim 45, wherein:

the solvent includes THF and AIBN;

the polymerization temperature is at least 50° C.;

the polymerization time is at least 1 hour; and the photosensitive polymer has a Mw of at least about 3,000 and a polydispersity of less than about 3.

47. A method of forming a photosensitive polymer according to claim 46, wherein:

the AIBN is present in an amount less than about 5 mol % based on the monomers;

the polymerization temperature is at least 65° C.;

the polymerization time is at least 4 hours; and the photosensitive polymer has a Mw of at least about 5,000 and a polydispersity of less than about 2.5.

48. A method of forming a photosensitive polymer according to claim 45, further comprising:

precipitating the polymer from the polymerization solution to obtain a precipitate;

dissolving the precipitate in THF to form a polymer solution;

precipitating the polymer from the polymer solution to obtain a second precipitate; and drying the second precipitate.

49. A photoresist composition suitable for forming patterns having a line/space pattern of less than 0.25 μm when exposed to light having a wavelength of 157 nm comprising:

a photosensitive polymer represented by a formula selected from a group consisting of

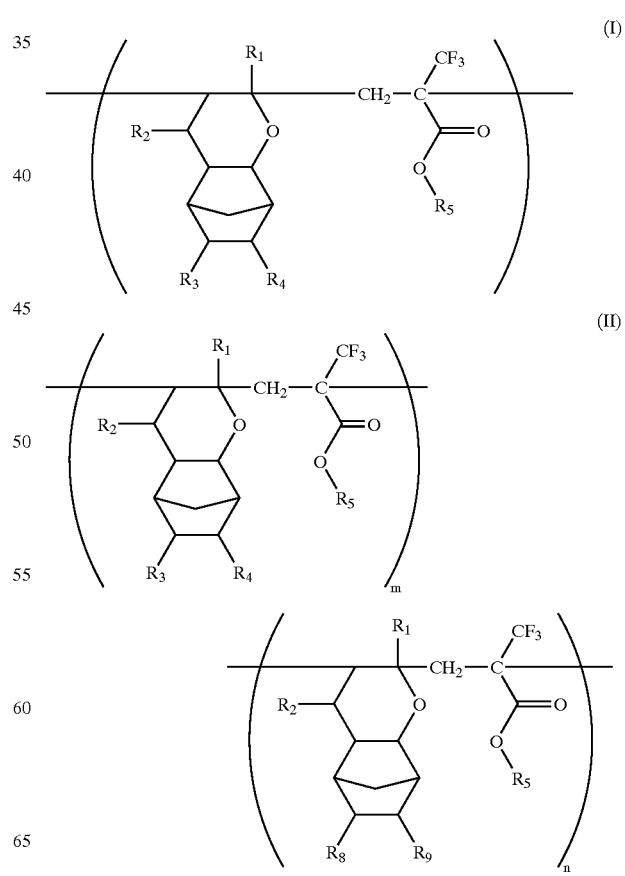

(IIB)

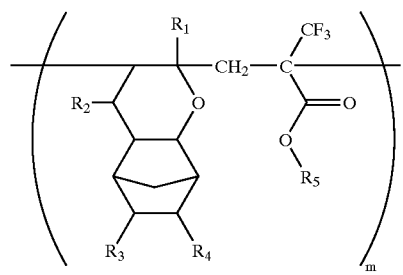

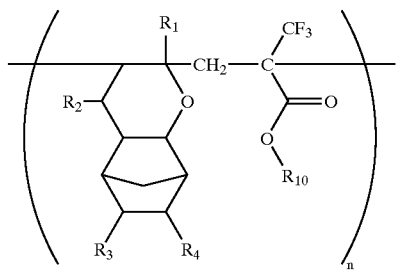

(III)

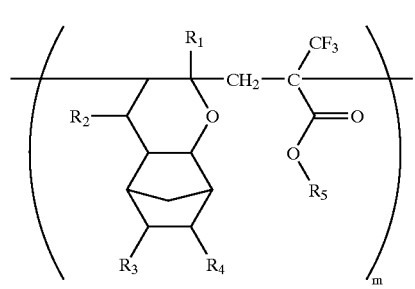

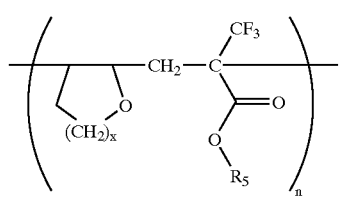

(IIIB)

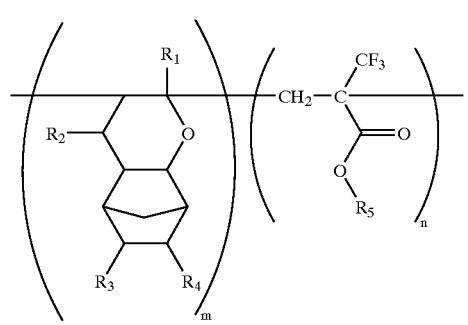

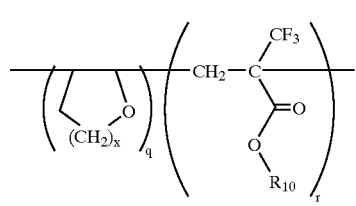

(IV)

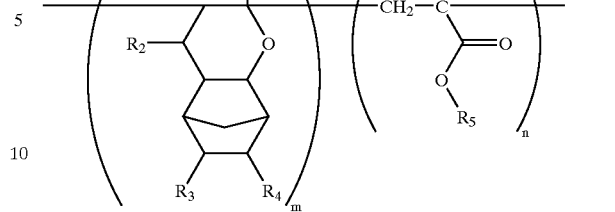

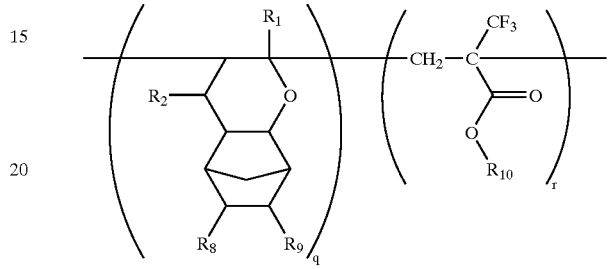

(V)

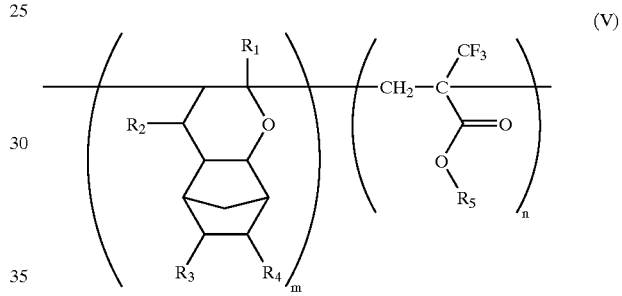

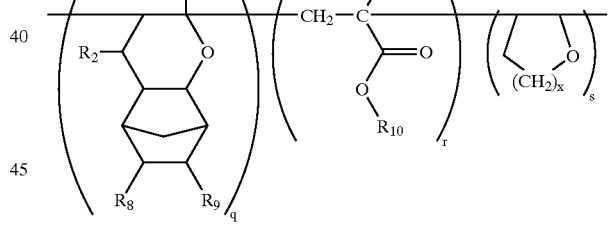

wherein x is 1 or 2;

m+q+s=n+r $R_1$ and $R_2$ are independently selected from a group consisting of hydrogen and methyl;

$R_3$, $R_4$, $R_8$ and $R_9$ are independently selected from a group consisting of hydrogen, hydroxy, alkyl, cycloalkyl, haloalkyl, alkoxy, carboxyl, carbonyl, ester and acid labile groups; and $R_5$ and $R_{10}$ are independently selected from a group consisting of hydrogen, hydroxy, alkyl, cycloalkyl, haloalkyl, alkoxy, carboxyl, carbonyl, ester and acid labile groups; and further wherein the polymer includes at least one monomer including an acid labile group; and a solvent.

50. A photoresist composition according to claim 49, wherein:

the acid labile group is selected from a group consisting of t-butyl, substituted cyclohexyl, 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl groups.

51. A photoresist composition according to claim 49, wherein:

the photosensitive polymer has a Mw of between about 3,000 and 100,000; and a polydispersity of between about 1.5 and about 3.0.

52. A photoresist composition according to claim 51, further comprising:

between about 1 and 30 wt % of a photoacid generator (PAG) selected from a group consisting of triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, PFOS (triphenylsulfonium perfluorooctanesulfonate), diphenyliodonium PFOS, methoxydiphenyliodonium PFOS, di-t-butyldiphenyliodonium triflate, N-hydroxysuccinimide PFOS, norbornene-dicarboximide PFOS and mixtures thereof;

between about 0.01 and 2 wt % of an organic base selected from a group consisting of triethylamine, triisobutylamine, triisooctylamine, triisodecylamine, diethanolamine, triethanolamine, N-alkyl substituted pyrrolidinone, N-alkyl substituted caprolactam, N-alkyl substituted valerolactam and mixtures thereof; and between about 30 and 200 ppm surfactant.

53. A photoresist composition according to claim 49, wherein:

the photosensitive polymer includes at least two different photosensitive polymers, each of which has a Mw of between about 3,000 and 100,000; and a polydispersity of between about 1.5 and about 3.0.

54. A photoresist composition according to claim 49, wherein:

the photosensitive polymer has a Mw of between about 7,000 and 25,000; and a polydispersity of between about 1.7 and about 2.3.

55. A photoresist composition according to claim 49, further comprising:

a photoacid generator (PAG).

56. A photoresist composition according to claim 55, wherein:

the photoacid generator includes a compound selected from a group consisting of triarylsulfonium salts, diaryliodonium salts, sulfonates and mixtures thereof.

57. A photoresist composition according to claim 56, wherein:

the photoacid generator includes a compound selected from a group consisting of triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, PFOS (triphenylsulfonium perfluorooctanesulfonate), diphenyliodonium PFOS, methoxydiphenyliodonium PFOS, di-t-butyldiphenyliodonium triflate, N-hydroxysuccinimide PFOS, norbornene-dicarboximide PFOS and mixtures thereof.

58. A photoresist composition according to claim 56, wherein:

the photoacid generator comprises between about 1–30 wt % of the photoresist composition based on the photosensitive polymer.

59. A photoresist composition according to claim 49, further comprising:

an organic base.

60. A photoresist composition according to claim 59, wherein:

the organic base includes a tertiary amine compound.

61. A photoresist composition according to claim 60, wherein:

the organic base includes one or more tertiary amine compounds selected from a group consisting of triethylamine, triisobutylamine, triisooctylamine, triisodecylamine, diethanolamine, triethanolamine, N-alkyl substituted pyrrolidinone, N-alkyl substituted caprolactam, N-alkyl substituted valerolactam and mixtures thereof.

62. A photoresist composition according to claim 61, wherein:

the organic base is present at a concentration of about 0.01 to 2.0 wt % based on the photosensitive polymer.

63. A photoresist composition according to claim 49, further comprising:

at least one surfactant.

64. A photoresist composition according to claim 63, wherein:

the surfactant is present within the photoresist composition in an amount between about 30 to 200 ppm.

65. A photoresist composition according to claim 49, wherein:

the photoresist composition is capable of forming patterns having line/space sizing of 0.25 µm or less when exposed to light having a wavelength of 157 nm at a light intensity of between about 10 and 30 mJ/cm$^2$.

66. A photoresist composition according to claim 65, wherein:

the photoresist composition is capable of forming patterns having line/space sizing of 0.15 µm or less when exposed to light having a wavelength of 157 nm at a light intensity of between about 10 and 30 mJ/cm$^2$.

67. A photoresist composition according to claim 65, wherein:

the photoresist composition is capable of forming patterns having line/space sizing of about 0.11 µm or less when exposed to light having a wavelength of 157 nm at a light intensity of between about 10 and 30 mJ/cm$^2$.

* * * * *